(12) United States Patent
Schertiger et al.

(10) Patent No.: US 9,549,839 B2
(45) Date of Patent: Jan. 24, 2017

(54) OSTOMY BAG WITH A FILTER CONSTRUCTION

(75) Inventors: Lars Olav Schertiger, Fredensborg (DK); Jan Torstensen, Virum (DK); Preben Luther, Birkerød (DK)

(73) Assignee: Coloplast A/S, Humlebaek (DK)

( * ) Notice: Subject to any disclaimer, the term of this patent is extended or adjusted under 35 U.S.C. 154(b) by 306 days.

(21) Appl. No.: 13/701,515

(22) PCT Filed: Jun. 1, 2011

(86) PCT No.: PCT/DK2011/050189
§ 371 (c)(1),
(2), (4) Date: Dec. 3, 2012

(87) PCT Pub. No.: WO2011/150936
PCT Pub. Date: Dec. 8, 2011

(65) Prior Publication Data
US 2013/0072886 A1  Mar. 21, 2013

(30) Foreign Application Priority Data

Jun. 4, 2010 (DK) .................................. 2010 70245
Jun. 4, 2010 (DK) .................................. 2010 70246
(Continued)

(51) Int. Cl.
*A61F 5/441* (2006.01)
*A61F 5/44* (2006.01)
*A61F 5/445* (2006.01)

(52) U.S. Cl.
CPC .............. *A61F 5/441* (2013.01); *A61F 5/4405* (2013.01); *A61F 5/445* (2013.01)

(58) Field of Classification Search
USPC ........................................................ 604/333
See application file for complete search history.

(56) References Cited

U.S. PATENT DOCUMENTS 4,274,848 A * 6/1981 La Gro ................................ 96/6
4,387,712 A 6/1983 Briggs et al.
(Continued)

FOREIGN PATENT DOCUMENTS

DE    20021420    3/2001
DE    20021420    9/2002
(Continued)

*Primary Examiner* — Tatyana Zalukaeva
*Assistant Examiner* — Guy K Townsend
(74) *Attorney, Agent, or Firm* — Coloplast Corp., Coloplast A/S; Nick Baumann

(57) ABSTRACT

An ostomy appliance comprising a pouch and a filter construction is provided. The filter construction has a first and second foil layer to provide an enclosure for the elements in the filter construction. The filter construction is attached inside the pouch so that the filter construction is free-hanging inside the pouch. The two foil layers may be generally parallel with the walls of the ostomy bag. The foil layers are provided with numerous holes functioning as gas-inlets for the filter construction. The filter construction includes a pre-filter element and a deodorizing filter. A method for collecting discharge as well as an ostomy appliance is provided. A method for reducing the number of balloonings and an ostomy appliance for reducing the number of balloonings is also provided. A method of increasing the time to ballooning as well as an ostomy appliance for increasing the time to ballooning is also provided.

30 Claims, 11 Drawing Sheets

(30) Foreign Application Priority Data

| | | |
|---|---|---|
| Nov. 8, 2010 | (DK) | 2010 70473 |
| Nov. 8, 2010 | (DK) | 2010 70475 |
| Nov. 8, 2010 | (DK) | 2010 70476 |
| Jun. 1, 2011 | (WO) | PCT/DK2011/050189 |
| Nov. 19, 2011 | (DK) | 2010 70498 |

(56) References Cited

U.S. PATENT DOCUMENTS

| | | | | |
|---|---|---|---|---|
| 4,490,145 | A * | 12/1984 | Campbell | 604/333 |
| 4,986,824 | A * | 1/1991 | Steer et al. | 604/333 |
| 5,306,264 | A | 4/1994 | Ferguson et al. | |
| 6,135,986 | A * | 10/2000 | Leisner et al. | 604/322 |
| 6,659,988 | B1 * | 12/2003 | Steer et al. | 604/333 |
| 7,341,578 | B2 * | 3/2008 | Bulow et al. | 604/333 |
| 8,178,746 | B2 * | 5/2012 | Hildeberg et al. | 604/360 |
| 8,298,201 | B2 * | 10/2012 | Albrectsen | 604/333 |
| 2005/0070863 | A1 * | 3/2005 | Bulow et al. | 604/332 |
| 2005/0085779 | A1 * | 4/2005 | Poulsen et al. | 604/332 |
| 2006/0271002 | A1 | 11/2006 | Botten | |
| 2007/0282284 | A1 * | 12/2007 | Mullejans et al. | 604/333 |
| 2008/0306459 | A1 * | 12/2008 | Albrectsen | 604/333 |
| 2009/0247970 | A1 * | 10/2009 | Keleny et al. | 604/333 |
| 2010/0010460 | A1 | 1/2010 | Butler | |
| 2010/0256581 | A1 * | 10/2010 | Albrectsen | 604/333 |
| 2010/0262097 | A1 * | 10/2010 | Hildeberg et al. | 604/359 |
| 2013/0072885 | A1 * | 3/2013 | Luther et al. | 604/333 |
| 2013/0072886 | A1 * | 3/2013 | Schertiger et al. | 604/333 |
| 2013/0218111 | A1 * | 8/2013 | Schertiger | 604/333 |

FOREIGN PATENT DOCUMENTS

| | | |
|---|---|---|
| DE | 20202711 | 9/2002 |
| EP | 0235928 | 9/1987 |
| EP | 0443728 A2 | 8/1991 |
| EP | 0607028 | 7/1994 |
| EP | 0981311 A1 | 3/2000 |
| EP | 1578308 | 9/2005 |
| GB | 2059797 | 4/1981 |
| GB | 2124086 A1 | 2/1984 |
| RU | 2077290 C1 | 4/1997 |
| RU | 2220685 C1 | 1/2004 |
| WO | 03020188 | 3/2003 |
| WO | 03071997 | 9/2003 |
| WO | 2006048019 A1 | 5/2006 |
| WO | 2007000168 A1 | 1/2007 |

* cited by examiner

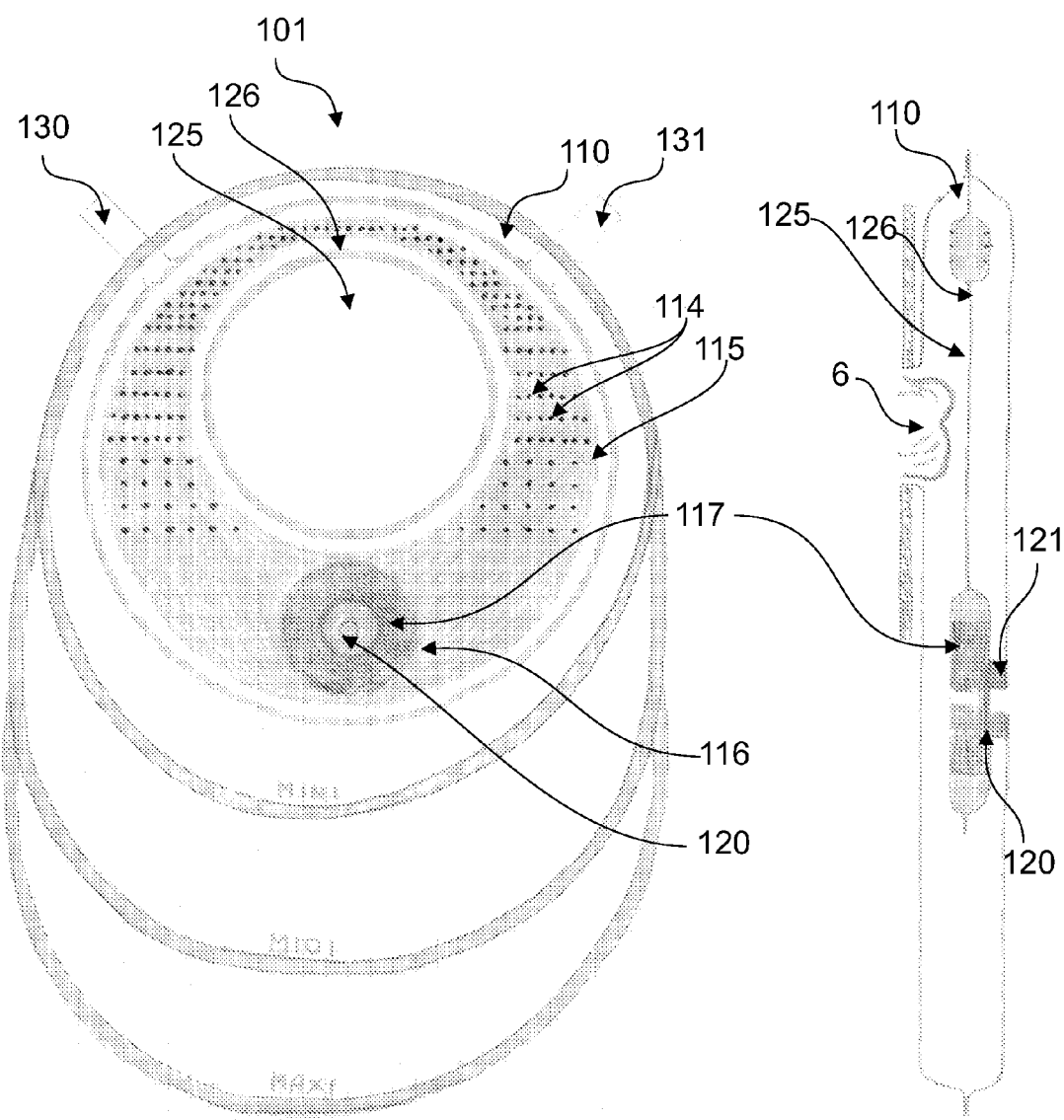

OSTOMY BAG WITH A FILTER CONSTRUCTION

The invention relates to an ostomy appliance having a filter construction enclosed in two foils, a first foil and a second foil. The filter construction is provided with holes at least in one of the foil layers and the holes function as gas-inlets. The invention also relates to a method of collecting discharge from a stoma, a method for reducing the number of balloonings and a method of increasing the time before ballooning occurs. Finally, the invention relates to an ostomy appliance for use in a method of collecting discharge, an ostomy appliance for reducing the number of balloonings and an ostomy appliance for increasing the time before ballooning occurs.

BACKGROUND

In connection with surgery for a number of diseases in the gastro-intestinal tract, one of the consequences in many cases is that the patient is left with an abdominal stoma, such as a colostomy or an ileostomy in the abdominal wall for the discharge of visceral contents. The discharge of visceral contents, including intestinal gases, cannot be regulated at will. For that purpose, the user will have to rely on an appliance to collect the material emerging from such opening in a bag, which is later emptied and/or discarded at a suitable time.

The discharge of flatus, measured in volume, may exceed the discharge of solid and liquid faecal matter by many hundreds of percent, and therefore there is usually the need for the continuous or frequent venting of the intestine or the collecting bag. Normally the out-flowing flatus is deodorised with a suitable filter. Commonly, the active filter is powdered active carbon, which absorbs $H_2S$ being the principal component of the smell of flatus.

During use of a collecting bag, the output from a colostomy or an ileostomy may stick on the face of the filter facing inwards in the collecting bag. This will eventually lead to clogging of the filter, thereby reducing the flow through the filter. When the filter is completely blocked, it will stop functioning and the bag will fill with gases and expand, an effect also known as ballooning. This may cause embarrassment to the user, as the bag will be noticeable through the clothing. It may also cause detachment of the appliance from the user's skin—or detachment of the pouch from the wafer.

SUMMARY OF THE INVENTION

The invention relates to an ostomy appliance with a filter construction. The pouch of the ostomy appliance has a front wall and a rear wall. The filter construction has a first and second foil providing an enclosure for the elements in the filter construction. The filter construction may be attached inside the pouch bag so that, in use, the filter construction is substantially free-hanging in the pouch, meaning that the filter construction is able to follow the movements of the pouch and further is able to crumble and curl during use. Holes are provided at least in one of the first or second foils so as to provide for gas-inlets to the filter construction. Such an ostomy appliance will in use be able to evacuate excess gas through the filter at any time because the provision of the free-hanging filter construction ensures that at least one inlet is always open.

BRIEF DESCRIPTION OF THE DRAWING

FIGS. 2 and 3 illustrate another embodiment of an ostomy appliance according to the invention.

In FIG. 1 the pouch is illustrated in the first configuration.

DETAILED DESCRIPTION OF THE INVENTION

Figure 1:
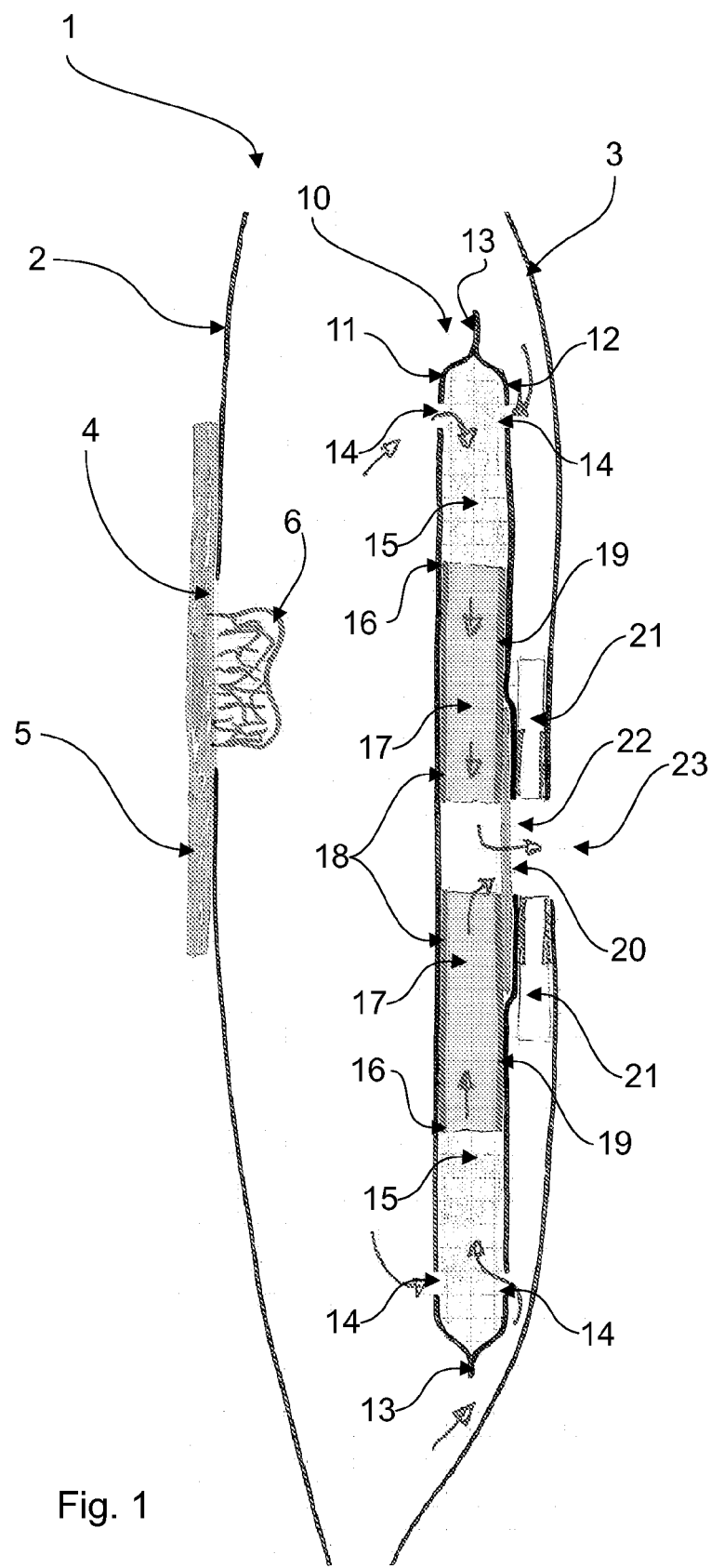
FIG. 1 illustrates an embodiment of an ostomy appliance according to the invention.

In a first aspect, the invention relates to an ostomy appliance comprising
  a pouch comprising
    at least one vent opening for letting gas exit the bag
    a filter construction comprising a first foil layer and a second foil layer defining an enclosure, the enclosure including a pre-filter element
      at least one gas-inlet being provided in at least one of the first and/or second foil layers
      at least one gas-outlet being provided in the second foil layer
wherein the second foil layer of the filter construction is attached to either the front wall or the rear wall of the pouch so that the gas-outlet of the filter construction communicates with the vent opening of the pouch and,
wherein the attachment is such that a major part of the filter construction is left free-hanging in the pouch.

An ostomy appliance with a filter construction as described above will have excellent properties for preventing or at least reducing ballooning because the filter construction is free-hanging in the pouch.

By free-hanging is meant that the filter construction is able to follow the movements of the pouch substantially unhindered. The filter construction may be attached only in the area immediately surrounding the vent opening leaving most (if not all) of the contour of the enclosure unattached to the ostomy appliance. Alternatively or additionally, the filter construction is attached in discrete points across the surface of the second foil. This means that in one embodiment, a major part of the filter construction is able to crumble and curl during use, thus keeping the filter construction from clinging to the walls of the pouch, and thus keeping at least some of the gas-inlet(s) open at all times. By crumbling and curling is meant that the filter construction obtains a wavy shape in the plane of the pouch.

In another embodiment, the free-hanging of the filter is so that the filter construction is cantilevered attached in the pouch.

By a major part of the filter construction is meant that the surface area of the part of the filter construction that is attached is significantly smaller than remaining surface area of the filter construction. For example, the attached area may constitute less than 20% of the surface area of the filter construction, such as 10% or 5% or even as little as 1%.

An ostomy appliance is well-known in the art. It usually comprises a pouch having a front wall and a rear wall of gas- and liquid impermeable foil-material (for example of polyethylene (PE), polyvinyl-chloride (PVC) or ethylene-vinyl-acetate (EVA)) that is welded or glued around the edges or the rim so as to form a pouch defining a waste collection chamber. The pouch may be welded or glued only partly around the rim so that an opening for emptying the pouch is provided at the bottom of the pouch. In that case, the pouch may be provided with means for closing that opening. The pouch usually includes a waste inlet opening which at the outer side is provided either with mechanical or adhesive coupling means for coupling to a body side wafer or with a skin-friendly adhesive adapted for direct adhering to the abdomen of the user.

Usually, the waste inlet opening is placed in the upper part of the ostomy pouch so that when a user stands up, the waste inlet opening will be above the midline of the ostomy pouch. This leaves a larger collecting volume below the waste inlet opening. Thus, the top of the ostomy appliance and the pouch is defined as the part closest to the waste inlet opening, and the bottom is defined as the opposite part. The longitudinal direction of the ostomy appliance and the pouch is defined as the direction from top to bottom. The transverse direction of the ostomy appliance, the pouch and filter construction positioned in the pouch is defined as the direction in the plane of the pouch perpendicular to the longitudinal direction. The axial direction is defined as the direction of the stoma.

The filter construction comprises a first and second layer of foil defining an enclosure for the filter construction. The first and second foil layers may be laminated to the surface of the elements (e.g. the pre-filter) in the filter construction. By laminated is meant that the foils are attached to the entire surface, so that there is no space between the elements and the foil layers. The foils may be attached by means of gluing or heat welding. When the first and second foil layers are laminated to the surface of the elements, the foil layers are not necessarily attached to each other along their contour as well. If the foil layers are un-attached at their contour, or at least partly unattached along their contour, the unattached parts also define gas-inlets to the filter construction.

Alternatively, the first and second foil layers may be attached to one another along their entire contour so as to define an enclosure. In this case, the pre-filter element may, during manufacturing, be compressed slightly in the cross-sectional direction of the filter construction. Compression of the pre-filter element ensures that there is no distance between the foils and the pre-filter element, thereby alleviating the risk of the liquid or semi-solid parts of output bypassing the pre-filter element. Thereby it is assured that the liquid material entering into the filter construction will flow through the pre-filter element.

The foil layers may be attached to each other by means of welding, which is a fast process to use in manufacturing. The foil in itself may thus be weldable. The foils may also be attached to each other by a gluing process, e.g. using acrylate and/or hot melt adhesive. Furthermore, the foil may be gas- and liquid-impermeable. A material such as PE-foil would be suitable for use. Alternatively, the foil may be non-woven or textile. However it has to be ensured that the liquid or semi-solid part of the output travels at least some distance through the pre-filter element before reaching the deodorising element. Therefore the foils immediately surrounding the deodorising element must be gas- and liquid-impermeable. In an embodiment, the gas- and liquid-impermeable foils may be provided in a distance of at least 3 cm from the deodorising element. In another embodiment, the gas- and liquid-impermeable foils may be provided in a distance of only 15 mm from the deodorising element. It depends on the type of output in the pouch, as described below.

In an embodiment, the filter construction includes a deodorising filter within the enclosure. Alternatively, the deodorising filter may be positioned on the outside surface of the pouch so that it communicates with the vent opening in the pouch. The deodorising filter may also be positioned inside the pouch communicating with the vent opening but outside the enclosure and communicating with the gas-outlet.

The deodorising filter may be provided as filter packages typically used for ostomy bags. Typically, the deodorising filter will have a foil layer laminated to the surfaces of the deodorising filter that is parallel to the gas-flow direction. This assures that gas is forced to flow in the intended gas-flow direction of the deodorising filter. Thus an adequate deodorising is achieved. The filter construction may include more than one deodorising filter, such as two or three. The number of vent openings in the pouch should correspond to the number of deodorising filters in the filter construction. As an example, a filter package having a shape and flow-path as Filtrodor® from Coloplast A/S may be used. This filter package comprises a disc-shaped foam element where the foam is impregnated in carbon. The foam element is covered with a gas-impermeable foil on both sides of the disc, except for a hole punched centrally in one of the foils. This hole functions as a gas-outlet to the deodorising filter and the periphery of the element functions as a gas-inlet. The gas-flow direction through the deodorising filter may also be opposite so that gas enters the deodorising filter centrally and exits at the periphery. When the gas has travelled the distance from the periphery of the disc to the centre (or vice-versa), it is adequately deodorised. The diameter of such an element may be approximately 20 to 25 mm but may be larger or smaller depending on the deodorising capacity.

The deodorising filter may also be of elongated shape with an inlet in one end and an outlet in the other. Such a deodorising filter may be of the type described in European Patent no. EP0235928B1.

The deodorising filter could be a carbon loaded porous material such as foam, felt, nonwoven or the like, or the activated carbon could be based on a carbonized material such as e.g. carbonized viscose or the like. The carbon could either be nonactivated or activated by applying catalyzing compounds such as copper oxide, chromium oxide, potassium permanganate or other catalyzing compounds.

In a preferred embodiment at least one of the first and/or second foil layers is provided with holes of a diameter of approximately 0.1-2.0 mm. Both foil layers may also be provided with holes. These holes function as gas-inlets for letting gas enter into the filter construction. The small size of the holes helps prevent semi-solid and to a certain degree liquid material from entering into the filter construction but allows gas to enter.

Holes in both foil layers minimise the risk of all of the inlets being covered by output from the stoma—even if the output should place itself near the filter construction in the bag. The position of the output depends on the user's movement (lying down or sitting up) and on the type of output. The output will typically at least sit near the rear wall of the ostomy bag. In this case, the holes in the foil facing the front wall will be accessible for gas. The output may also sit near the front wall and in this case, the holes in the foil facing the rear wall will be accessible for gas.

The holes may be made by punching, burning, and etching or by use of a laser, drill, needle or dinking die. The number of holes may be anything between 1 hole for an ileostomy bag up to more than 150 holes for a colostomy bag. The number of holes depends on the size of the filter construction and the type of output exiting the stoma.

The filter construction of this invention is contemplated to be used in connection with an ileostomy as well as a colostomy. The two types of stomas typically deliver different types of output. For an ileostomy the output is typically thinner and more syrupy whereas the output from a colostomy is typically more like porridge. However, the type of output may also depend on the intake of food and liquids—therefore, we will in the following refer to thin output (syrupy to liquid) and thicker output (like porridge) irrespective of whether it comes from an ileostomy or a colostomy.

For thicker output, there is a risk that the holes, functioning as gas-inlets, will be clogged due to smearing of the output over the holes. Because the output has a relative thick consistency it may not be able to pass completely through the hole. Therefore, the hole may be filled with output and thus stop functioning as gas-inlet. For thin output, the holes will not be filled with output and thus clogged because the output will be able to pass through the holes. Therefore, a larger number of holes (gas-inlets) are needed for thick output than for thin output. For thin output the number of holes (gas-inlets) may be 2 or only 1 hole (gas-inlet), whereas for thick output up to 150 holes (gas-inlets) may be used. At least more than 50 holes (gas-inlets) may be used for thick output.

Not only the number of holes but also the size of the holes may depend on the type of output. This is because it is unlikely that thick output would be able to pass through a hole (gas-inlet) because these holes are typically below 2 mm in diameter. On the other hand it is unlikely that a small hole would be able to stop thin output. Therefore, for thin output few and larger holes (gas-inlets) are preferred and for thick output many and small holes (gas-inlets) are preferred.

When the size of the holes is given as a diameter size, the reference is to a largest diameter of the hole in case the hole is not circular but rather elliptical. If the hole is more angular, then the reference is, again, to a largest "diameter" which in this case may be the longest diagonal dimension across the hole.

In an embodiment of the invention, a first distance between two neighbouring holes is so that liquid cannot travel from one hole to the neighbouring hole within the normal use time. In a related embodiment, a second distance from the deodorising element to the nearest gas-inlet is so that liquid cannot travel from the nearest gas-inlet to the deodorising element within the normal use time.

Throughout the application, whenever referring to a first distance between the holes or a second distance between the gas-inlets and the deodorising element, these distances are in the planar direction of the filter construction. Thus, the second distance is defined as the distance in a direction in the plane of the foils of the filter construction from the gas-inlet closest to the deodorising filter to the edge of the deodorising filter closest to the same gas-inlet. The planar direction is defined by the foil layers of the filter construction so that each foil extends in the planar direction.

For thick output, it is contemplated that the clogging of the filter construction occurs when all gas-inlets are blocked by output. The gas-inlets may be blocked by semi-solid material smeared across the hole thereby closing the hole. The first distance between neighbouring holes and the second distance from the gas-inlets to the deodorising element ensures that output clogging one hole will not be able to travel through the pre-filter material along the surface of the foil and into the next hole or into the deodorising element and clogging that as well. Liquid and semi-solid matter entering into the deodorising element may leave this element bereft of its ability to deodorise the flatus gas. Tests have shown that if the first distance between two gas-inlets or the second distance from a gas-inlet to the deodorising element is more than 10 mm in the planar direction, then semisolid or liquid matter will not be able to travel through the pre-filter material within the normal use time. Likewise, these distances minimise the risk of smearing of output across the surface of the filter construction from covering too many of the gas-inlets.

The second distance is in an embodiment at least 5 mm. Only a small amount of liquid will be able to enter into the pre-filter element because of the small holes in the foils of the filter construction, thus only a short distance is needed to be able to stop this liquid. However, the second distance may also be approximately 3 cm. Again there is a difference between thin and thick output. Thick output will not be able to travel very far into the pre-filter element, therefore the second distance between the gas-inlets and the deodorising filter may be rather low, for example as low as 5 mm. In an embodiment, the smallest distance between the deodorising element and a gas-inlet is more than 15 mm. Thereby it is ensured that no liquid or semisolid matter will reach the deodorising element during the normal use time.

However, thin output will be able to travel farther through the pre-filter element, therefore the second distance between the gas-inlets and the deodorising filter should be longer, for example at least 3 cm.

A third distance between gas-inlets and the rim of the filter construction may be more than mm. When the gas-inlets are near the rim of the filter construction, there is no neighbouring hole in the direction of the rim. Therefore, the distance may be smaller here.

The foil enclosure defining the filter construction may be provided with a drainage opening facing downwards in the ostomy bag—that is facing towards the bottom of the ostomy bag. This bottom facing drainage opening provides an opportunity for particularly thin output to be drained out of the filter construction. The opening may be provided with a one-way valve so that output in the bag is prevented from entering into the filter construction through this opening. A one-way valve is well-known in the art and may for example be provided as a foil valve.

In an embodiment, the filter construction further includes a flange surrounding the gas-outlet. The filter flange may be an injection moulded flange. This filter flange serves the purpose of providing an element for welding the filter construction to the ostomy bag. Thereby, the positioning of the filter construction is independent of the production of the ostomy bag and can be done either during production of the ostomy bag or at any time afterwards. Furthermore, the filter flange is made of a material that is substantially non-conductible and able to absorb heat. Therefore the heat from the welding process is not transferred to the filter construction. Thus, the filter construction can be manufactured as a finished element, including the pre-filter element and the deodorizing filter, and subsequently welded to the bag without risking that the foils and pre-filter element are welded to each other.

The filter flange may be made of a material such as PE or EVA which materials both are able to quickly weld to the ostomy bag. The welding can be done at for example 160° C. for approximately ½ second. The thickness of the flange should be above approximately 0.5 mm to be able to absorb the heat from welding so as to prevent the foils and the pre-filter element from welding to each other. The upper limit for the thickness is controlled by the requirement for a discreet bag—therefore it should be below approximately 1 mm.

The filter flange may be glued to the bag instead of welded to it. This may be done using an acrylate or hot melt adhesive.

The filter construction may also be directly welded to the ostomy bag, meaning that the filter flange may be omitted. In this case the deodorising filter is directly welded to the bag, that is, the foil that covers the deodorising filter is welded to the front or rear wall of the ostomy bag.

The foils covering the deodorising filter may in an embodiment of the invention be made of a three-layer foil structure laminated to the deodorising filter. In this case the foils may be made of gas impermeable and liquid impermeable barrier foils, so that gas and liquid are prevented from exiting the filter at any other position than the defined gas-outlet. The three-layer structure may be made of an outer foil layer, which is adapted to be welded to the bag foil, an intermediate foil layer adapted to function as an intermediate protective layer and an inner foil layer adapted to be laminated to the deodorising filter. The intermediate layer protects the foil structure from pin-holes occurring through the layers. The protective ability is provided by ensuring that the intermediate foil layer has a significantly higher melting temperature than the outer and inner foil layers. For example, the outer and inner foil layers may have a melting temperature between 80° C. and 150° C. and the intermediate layer may in that situation have a melting temperature above 200° C. As an example, the outer and inner layer may be made of a copolymer of Ethylene-Vinyl-Acetate (EVA) and Poly-Ethylene (EVAPE) and the intermediate layer may be made of Poly-Amide (PA).

A three-layer structure, as described, may be welded or laminated to the side of the deodorising filter facing outwards when positioned in the ostomy bag. On the side facing inwards in the bag, the avoidance of pin-holes and the gas impermeability is less important because gas leaking through the foils will only re-enter the ostomy bag. However, the three-layer foil structure may nevertheless be used on the inside as well, thereby avoiding the need for using separate foils. Anyhow, leakage of gas towards the outside is to be avoided.

When foil-layers, as described above, are used as cover layers for the deodorising filter, this filter may in itself serve as a heat-absorbable flange, because the deodorising filter is able to absorb the heat from the welding process.

The pre-filter element may be made of foam material, for example of PE or poly-urethane (PU). The pore size may be between 15 and 100 PPI, such as 30 or 45 PPI. PPI is a unit giving a measure for the pore size although it actually refers to the number of pores per inch in the foam material. Felt, fluff, nonwoven or any other porous material may also be used. Gas (including solid and/or semi-solid waste material) will enter into the pre-filter element through the holes in the foil layers that provides the gas-inlets to the filter construction. Due to the tortuous structure of the foam, most of the liquid and semi-solid waste will be captured in the foam leaving only gas to pass through the foam to reach the deodorising filter.

The thickness of the pre-filter element may be between 1 and 5 mm such as approximately 2 or 3 mm. The thickness is defined as the dimension in the direction across the filter construction corresponding to the dimension of the pre-filter element in the direction from the first foil layer towards the second foil layer.

The area of the pre-filter element may be so large that it has almost the same area as the front or rear wall of the pouch. However, room should be left for manufacturing tolerances. The area of the pre-filter element may be as low as 10% of the area of the front or rear wall when taken in the plane of the pouch. This will be the case if a large pouch is used, for example a Maxi-pouch. In another embodiment, the area of the pre-filter element may be up to 80 or 90% of the area of the front or rear wall of the pouch. This may particularly be true for small pouches, for example a Mini-pouch.

A large pre-filter element may be advantageous for bags filled with thin output, because it is difficult to completely prevent thin output from entering into the pre-filter element. Thus a large volume of foam is needed to prevent the thin output from reaching the deodorising filter. A large pre-filter element may also be advantageous for bags filled with thicker output, because a large number of gas-inlets are needed to ensure that at least some gas-inlets are open. As mentioned earlier, when thick output is present in the bag, the gas-inlets will be blocked because of the smearing of the output over the inlet holes. Thus a large area of foil provided with gas-inlets is needed, when the bag is filled with thick output.

The gas-outlet of the filter construction communicates with the vent opening in form of a hole or slit in the ostomy bag so that gas exiting the gas-outlet enters through the vent opening and out in the ambience or through the deodorising filter if this is positioned on the outside of the pouch. The communication may be done by positioning the gas-outlet in alignment with the vent opening or at least in the near vicinity of the vent opening. The vent opening should be enclosed, for example by a weld surrounding the vent opening, so that gas from the pouch is prevented from exiting the vent opening without having passed through the filter construction. Typically, this can be ensured by welding the filter construction to the ostomy pouch in an uninterrupted weld, so that the gas-outlet and the vent opening lie within the boundaries of the weld.

In an embodiment of the invention, the filter construction further includes a membrane positioned at the gas outlet. This membrane is gas-permeable, but moisture-impermeable. The membrane may be microporous and hydrophobic and made of a material like Goretex® or Tyvek®. The membrane should be able to provide a flow through of between 100 to 550 ml/min at 0.01 bar pressure difference, for example 250 ml/min or 350 ml/min.

The membrane may be attached, e.g. adhered, to the surface of the deodorising filter, i.e. between the surface of the deodorising filter and the "inner" surface of the second foil. Alternatively, the membrane is positioned on the outside of the second foil—that is between the gas-outlet and the vent opening on the pouch.

The foil layers of the filter construction may enclose the pre-filter element, the deodorising filter and the membrane.

In one embodiment, where the enclosure includes the deodorising filter, the pre-filter element comprises a cut-out for the deodorising filter. The cut-out may be disc-shaped to match a disc-shaped deodorising filter. The gas inlets are placed near the periphery of the filter construction and the deodorising filter has its gas-inlet along the periphery of it and a substantially centrally placed outlet.

The pre-filter element may be provided as an annular foam-element. It may have a circular or angular outer periphery. A part (for example the central part) of the pre-filter element is removed by punching or cutting a cut-out in the pre-filter element thereby leaving room for the deodorising filter. Preferably, the cut-out for the deodorising filter substantially matches the outer contour of the deodorising filter. If the deodorising filter is disc-shaped, then the cut-out for the deodorising filter is generally disc-shaped and if the deodorising filter is angular or banana-shaped, the cut-out for the deodorising filter will be provided with generally that shape. Matching the cut-out for the deodorising filter with the deodorising filter provides a more compact structure. Gas entering into the filter construction through the gas-inlets at the periphery will travel through the pre-filter element towards the inner periphery of the pre-filter element and from there into the deodorising filter. Then the gas will travel transversely through the deodorising filter and exit the filter construction at the opening in one of the foil layers providing the gas-outlet. A filter construction like that will be compact and easy to position anywhere in the ostomy bag according to production need or setup.

In an embodiment, the pre-filter element is positioned next to the deodorising filter so that they are positioned juxtaposed each other within the filter construction. In such a construction the deodorising filter will be positioned at one end of the filter construction. The pre-filter and the deodorising element may, in other words, be positioned sequentially. The filter construction may thus be elongated and preferably slightly curved so that it can follow the contour of the ostomy bag. In one related embodiment, the pre-filter element and the deodorising filter are positioned in the same plane. Alternatively, the deodorising filter is positioned atop the pre-filter element.

An embodiment of the invention relates to the filter construction incorporating an inspection window allowing the user visual access to the stoma and possibly also the peristomal area.

This inspection window may be provided in the pre-filter element so that the pre-filter element is a generally disc-shaped element having a circular hole with a diameter of at least the diameter of the waste inlet opening, where the foil layers of the filter construction are welded along the periphery of the circular hole in the pre-filter element.

To provide a see-through inspection window, either the foil layers need to be transparent or they need to be removed in the circular hole.

In a related embodiment, the inspection window is placed off-centre in the pre-filter element and the deodorising filter is placed in a cut-out for the deodorising filter.

The inspection window may be placed so that it leaves a thin strip of pre-filter element above the waste inlet opening and a larger area with the cut-out for the deodorising filter below the waste inlet opening. Thereby, the deodorising filter will be placed below the waste inlet opening. However, the inspection window may also be placed so that a thin strip of the pre-filter element is below the waste inlet opening and the larger area including the cut-out for the deodorising filter and the deodorising filter is placed above the waste inlet opening.

The stoma-inspection window allows a user to inspect the stoma and the peristomal area from the outside of the ostomy appliance. This requires that part of the front wall of the pouch is transparent. The diameters of the individual parts may in a specific embodiment be as follows: the deodorising filter, 30 mm, the pre-filter element, 110 mm and the inspection window in the pre-filter element, 70 mm.

In another embodiment, the inspection window may be provided because the pre-filter element is banana-shaped and positioned above the stoma and thus not in the way of viewing the stoma. The pre-filter element may be placed above and partly around the waste-inlet opening. This pre-filter element may have a circular hole in the middle of the banana-shape to provide room for the deodorising filter.

An embodiment of the invention relates to providing a filter flap as described in European Patent EP1578308B1 in an ostomy appliance according to this invention. Thereby it is assured that should the flow through the filter construction of this invention be too high, so that the front and rear wall of the pouch begins to collapse towards each other resulting in pancaking, then it is possible to partly or completely close the vent opening of the pouch with the flap described in the patent.

In a second aspect, the invention relates to an ostomy appliance comprising
  a pouch including a front wall and a rear wall,
  a waste inlet opening in the rear wall for letting the output from the stoma enter into the pouch,
  at least one vent opening for letting gas exit the bag,
  a filter construction comprising a first and second layer of foil defining an enclosure,
    the filter construction being attached inside the pouch so that each of the foil-layers are substantially parallel to the front and rear wall of the pouch, the first layer of foil facing the rear wall and the second layer of foil facing the front wall of the pouch,
    the filter construction being provided with gas-inlets at least in one of the foil layers, and a gas-outlet placed in the second foil adapted for communicating with the vent opening,
  the enclosure including a pre-filter element.

An ostomy appliance with a filter construction, as described above, will be able to evacuate the gas from the bag at all times. The provision of the gas-inlets in one of the foil layers or in both layers provide for pathways through the pre-filter at all times. Furthermore, the position of the foils parallel to the front and rear wall helps minimise the risk of covering the gas-inlets with output during use.

In an embodiment an ostomy appliance according to the second aspect of the invention includes a deodorising filter positioned inside the enclosure so that gas exiting the pre-filter element enters directly into the deodorising filter and from there out through the gas-outlet. A gas flow direction is defined as the direction in which the gas flows from the gas-inlets through the pre-filter element, through the deodorising filter and out through the gas-outlet and vent opening.

In an ostomy bag according to the second aspect of the invention, the filter construction may comprise one or more carrying means attached to the bag foils at the time of the contour welding process step.

The carrying means may be separate or integral parts of one or both of the foil layers of the filter construction; if separate they may be attached to the foil layer(s) by welding or gluing. The carrying means may attach the filter construction to the contour of the ostomy bag in the upper part thereof so that during use, gravity aids in forcing the filter construction downwards into the bag and keeping it in a desired position. The carrying means may also attach the filter construction in a lower position, if this is desired.

The filter construction will thus be prevented from being torn off inside the bag during use. To a certain extent, the filter construction will still be able to crumble during use. This is because the carrying means only attach the upper part of the filter construction to the ostomy bag. Thus, the lower part of the filter construction may still be free-hanging.

In a third aspect of the invention, the invention relates to an ostomy appliance comprising
    a pouch comprising
        a front wall and a rear wall
        a waste inlet opening in the rear wall for letting the output from the stoma enter into the pouch
        at least one vent opening for letting gas exit the bag
    a filter construction attached to the ostomy bag and comprising a first foil layer and second foil layer defining an enclosure, the enclosure including a pre-filter element
        multiple gas-inlets being provided in at least one of the first and/or second foil layers
        a gas-outlet being provided in the second foil layer,
wherein the filter construction is adapted to crumble when the bag is filled.

An ostomy appliance with a filter construction, as described above, will be able to evacuate the gas in the pouch at all times. The positioning of the gas-inlets at the foil layer(s) of the filter construction and the ability of the filter construction to crumble ensures that at least one inlet is open at all times particularly when the pouch is filled or ballooning occurs in the pouch. When the pouch fills up, the bag will change shape towards a more blown up, longitudinal configuration. This means that the lower part of the pouch may move slightly downwards due to the load in the pouch and at the same time or alternatively, the pouch may be thicker in the axial direction (outwards in direction of the stoma). This leads to a decrease in the width direction and will lead to crumbling of the filter construction.

In an embodiment of the invention according to the first, second or third aspect, the filter construction obtains a crumbling when the pouch is filled as a result of the relationship between the width of the filter construction and the width of the pouch in the transverse direction.

By adapting the width of the filter construction in the transverse direction to the width of the pouch in the transverse direction it is possible to achieve that the filter construction crumbles when the pouch is filled. During use, the configuration of the pouch moves between two extreme configurations:
    a first configuration in which the pouch is neither distended nor inflated
    a second configuration in which the pouch is distended and/or inflated.

During filling of the pouch and as long as the filter is able to handle the amount of gas, the pouch may assume any configuration between the first and second configuration.

This means that in the first configuration of the pouch, the width of the pouch is substantially unaltered when compared to the original width of a new, un-used pouch. In the second configuration of the pouch, the width of the pouch is reduced compared to the original width of a new, un-used pouch.

In an embodiment of the invention according to the first, second or third aspect, the filter construction has a width in the transverse direction which is at least 100%, such as at least 80% or at least 60% of the width of the pouch in the transverse direction.

The width of the filter construction is meant to be the largest width across the filter construction in the transverse direction in the plane of the foil layers. Likewise, the width of the pouch is the largest width across the bag in the transverse direction, in the plane of the walls of the pouch.

When the filter construction has a width corresponding to the pouch—and the filter construction is entered into the pouch—then the filter construction will obtain a wavy shape or curl slightly as soon as it is entered into the pouch. This will assist in providing access to the gas-inlet(s) positioned across the surface of the filter construction.

It is contemplated that, in the second configuration of the bag, the width of the pouch is reduced. By providing a width of at least 80% of the width of the pouch a filter construction that can be easily mounted inside the pouch is obtained, because the difference in width leaves room for attaching the filter construction to either the front or rear wall of the pouch and then subsequently attaching the front or rear wall to each other along their rim by any known means. Thus the 80% provides for the manufacturing tolerances of the filter construction and the pouch, while still providing a filter that is able to curl when the pouch is filled or balloons, because the width of the pouch is reduced to below 80% of the original width of a new, un-used pouch.

By providing a width of at least 60% of the width of the pouch, the same effect as above is achieved—leaving a little more room for manufacturing tolerances and providing a filter construction that will require at little more filling or ballooning in the pouch before it is able to curl.

For the second and third aspect of the invention, all other parts of the ostomy appliance and filter construction may be as described under the first aspect of the invention above. For example an ostomy appliance according to the second or third aspect of the invention may also include deodorising filter positioned inside the enclosure, outside the pouch or between the enclosure and the pouch wall. Similarly, an ostomy appliance according to the second or third aspect may also include holes functioning as gas-inlets of approximately 0.1-2.0 mm in diameter and in a number of for example 2 for an ileostomy bag up to more than 150 for a colostomy bag. Likewise, in an ostomy appliance according to the second or third aspect of the invention, the ostomy appliance itself, the distance between the gas-inlets and between the gas-inlets and deodorising filter, the filter flange, the welding of the filter construction to the wall of the pouch, the pre-filter element, the deodorising filter, the gas-outlet and vent, the membrane, the provision of the different parts of the filter construction including their mutual position and the inspection window may be provided as described above.

A particularly interesting embodiment of the invention relates to an ostomy appliance according to the first second or third aspect and
    wherein the gas-inlets have a diameter of at least one 1 mm such as approximately 2 mm and,
    wherein the area of the pre-filter element is larger than 40% of the area of the rear wall.

Such an ostomy appliance is particularly useful for use with an ileostomy, because it has few, large holes and a large area of pre-filter element. Thus it utilises the fact that it is not possible to prevent thin output from entering into the pre-filter, but the pre-filter element is large enough to be able to contain it through-out the normal wear-time for ileostomy bags. The large holes make it (almost) impossible for the thin output from an ileostomy to clog the holes by smearing output over them.

By providing an area of the pre-filter element larger than 40% of the area of the rear wall an adequate amount of porous material will be present even if the porous material is only 5 mm in thickness. This will still leave an adequate volume of porous material so that the pre-filter element is able to handle the amount of liquid entering into the pre-filter element.

Another interesting embodiment of the invention relates to an ostomy appliance according to the first second or third aspect and
- wherein the number of gas-inlets is more than 50 and provided in both the first and second foils,
- wherein the gas-inlets comprise holes having a diameter below 1 mm, such as approximately 0.5 mm as well as holes having a diameter of approximately 1 mm or more, such as approximately 2 mm.

Such an ostomy appliance is particularly useful for use with a colostomy because most of the output coming out of a colostomy is rather thick and thus, as described above, the filter construction will be clogged because the output gets smeared across the surface of the filter construction—therefore, the number of holes needs to be large and positioned in both foils so as to prevent all of them from being clogged. Furthermore, output coming out of a colostomy may comprise thinner output as well—therefore it is advantageous if the diameter of the gas-inlets varies.

In a fourth aspect of the invention, the invention relates to a method of collecting ostomy discharge in an ostomy appliance comprising a pouch and a filter construction comprising a first foil layer and a second foil layer defining an enclosure, the enclosure including a pre-filter element, wherein multiple gas-inlets are provided in at least one of the foil layers, a gas-outlet being provided in the second foil layer, the filter construction being attached inside the pouch so that a major part of the filter construction is left free-hanging in the pouch, the method comprising placing the appliance around the stoma.

In an embodiment, the pouch is provided with a vent opening and the filter construction is positioned so that the gas-outlet of the filter construction communicates with the vent opening of the pouch.

A fifth aspect relates to an ostomy appliance comprising a pouch and a filter construction, comprising a first foil layer and a second foil layer defining an enclosure, the enclosure including a pre-filter element, wherein multiple gas-inlets are provided in at least one of the foil layers, a gas-outlet being provided in the second foil layer, the filter construction being attached inside the pouch so that a major part of the filter construction is left free-hanging in the pouch, for use in a method of collecting ostomy discharge, the method comprising placing the appliance around the stoma.

In an embodiment, the pouch is provided with a vent opening and the filter construction is positioned so that the gas-outlet of the filter construction communicates with the vent opening of the pouch.

In an embodiment of the above fourth and fifth aspect, the ostomy discharge is collected during the night.

A method and an ostomy appliance as described in the fourth and fifth aspect allows a user to sleep through most of the night because they will not be disturbed by ballooning of their ostomy bag.

In a sixth aspect of the invention, the invention relates to a method of reducing the number of ballooning(s) occurring in an ostomy appliance comprising a pouch and a filter construction comprising a first foil layer and a second foil layer defining an enclosure, the enclosure including a pre-filter element, wherein multiple gas-inlets are provided in at least one of the foil layers, a gas-outlet being provided in the second foil layer, the filter construction being attached inside the pouch so that a major part of the filter construction is left free-hanging in the pouch, the method comprising placing the ostomy appliance around a stoma.

In a seventh aspect of the invention, the invention relates to an ostomy appliance comprising a pouch and a filter construction comprising a first foil layer and a second foil layer defining an enclosure, the enclosure including a pre-filter element, wherein multiple gas-inlets are provided in at least one of the foil layers, a gas-outlet being provided in the second foil layer, the filter construction being attached inside the pouch so that a major part of the filter construction is left free-hanging in the pouch, for use in a method of reducing the number of ballooning(s) occurring in an ostomy appliance, the method comprising placing the ostomy appliance around a stoma.

Clinical tests have shown that ostomy appliances according to this invention are able to reduce the number of balloonings occurring by more than 50%—se the paragraph below. This means that a user will be less bothered by balloonings when wearing an ostomy appliance according to this invention, thus leading to fewer embarrassing situations occurring and fewer detachments of the pouch from the wafer or of the appliance from the skin of the user.

In an eighth aspect of the invention, the invention relates to a method of increasing the time before ballooning occurs in an ostomy appliance comprising a pouch and a filter construction comprising a first foil layer and a second foil layer defining an enclosure, the enclosure including a pre-filter element, wherein multiple gas-inlets are provided in at least one of the foil layers, a gas-outlet being provided in the second foil layer, the filter construction being attached inside the pouch so that a major part of the filter construction is left free-hanging in the pouch, the method comprising placing the ostomy appliance around a stoma.

In a ninth aspect of the invention, the invention relates to an ostomy appliance comprising a pouch and a filter construction comprising a first foil layer and a second foil layer defining an enclosure, the enclosure including a pre-filter element, wherein multiple gas-inlets are provided in at least one of the foil layers, a gas-outlet being provided in the second foil layer, the filter construction being attached inside the pouch so that a major part of the filter construction is left free-hanging in the pouch, for use in a method of increasing the time before ballooning occurs in an ostomy appliance, the method comprising placing the ostomy appliance around a stoma.

Clinical tests have shown that ostomy appliances according to this invention are able to increase the time before a ballooning occurs with more than 70%—see the paragraph below. This means that a user will be able to wear an ostomy appliance according to the invention for a longer time before having problems with ballooning. This may lead to a better and more un-interrupted sleep at night, because the user does not have to get up to let air out of the ostomy appliance.

In an embodiment of the sixth, seventh, eighth or ninth aspect of the invention, the ostomy appliance is placed around a colostomy and the first and second foil layers are provided with gas-inlets in a number exceeding 50. The number of gas-inlets for use with a colostomy may also be more than 75, such as more than 100 and even more than 150 holes.

In another embodiment of the sixth, seventh, eighth or ninth aspect of the invention, the ostomy appliance is placed around an ileostomy and at least one of the foil layers is provided with at least one gas-inlet of a diameter of at least 1 mm and the pre-filter element has a volume large enough to handle the liquid output entering into the pre-filter element through-out the normal wear time. The number of gas-inlets may in this embodiment be 2 holes.

A volume large enough to handle the liquid output means that the thickness of the pre-filter (in the axial direction of the stoma) is at least 5 mm and the area of the pre-filter in the plane of the filter construction is at least 40% of the area of the rear wall.

Other aspects of the ostomy appliance as described above may also be combined with the fourth to ninth aspect of the invention.

Clinical Tests

Ostomy appliances as described above have been tested by users having a colostomy (20 users) and users having an ileostomy (20 users). The tests have been compared to reference ostomy appliances comprising two filter constructions each with a pre-filter of porous material 50 mm×10 mm×3 mm and a deodorising filter of carbonised foam 30 mm×7 mm×3 mm. The study was designed as an open, randomised cross-over study. All users were using one-piece ostomy appliances and should usually experience ballooning problems at least once a week. The users were instructed to change the ostomy appliance when they experienced ballooning and should otherwise follow the normal changing pattern.

Both types of users experienced an increase in the time before ballooning occurred and a decrease in the number of balloonings occurring.

For colostomy users, the number of reference ostomy appliances tested was 567 appliances and the number of ostomy appliances according to this invention was 526 appliances. The number of balloonings in the reference appliances was 129 and the number of balloonings in the appliances according to this invention was 59. Thus the number of balloonings experienced by the appliances of this invention was decreased by 52%.

For ileostomy users, the number of reference ostomy appliances tested was 294 appliances and the number of ostomy appliances according to this invention was 283 appliances. The number of balloonings in the reference appliances was 161 and the number of balloonings in the appliances according to this invention was 74. Thus the number of balloonings experienced by the appliances of this invention was decreased by 62%.

Colostomy users testing the reference appliances experienced in average ballooning approximately every 1.5 day (0.72 balloonings/per user/per day). When the same users tested the ostomy appliances according to this invention, they experienced in average ballooning approximately every $4^{th}$ day (0.26 balloonings/per user/per day). Thus the time before ballooning occurs increased by 74%.

Ileostomy users testing the reference appliances experienced in average ballooning almost every day (0.90 balloonings/per user/per day). When the same users tested the ostomy appliances according to this invention, they experienced in average ballooning approximately every $3^{rd}$ day (0.34 balloonings/per user/per day). Thus the time before ballooning occurs increased by 82%.

Example

Testing of Filter Construction

The testing was performed using a filter tester apparatus that can hold an ostomy bag (=ostomy appliance) while pressure and airflow is monitored. The apparatus includes a differential pressure meter to monitor the pressure and a flow controller to monitor the airflow. Additionally, the apparatus can apply a controlled simulation of a contamination event for an ostomy bag filter. The filter tester apparatus applies a controlled massaging and shaking of an ostomy bag containing a simulated colo- or ileo-output. The simulated colo-output has a consistency like porridge and the simulated ileo-output has a consistency like syrup.

The testing was carried out by mounting an ostomy bag containing simulated Colo-output medium in the filter tester apparatus. Following this, the ostomy bag was inflated to 10 mbar. When the pressure was stable at 10 mbar, the flow through the uncontaminated filter construction was determined by reading the value at the flow controller.

When the uncontaminated flow had been noted, the ostomy bag was deflated and the first contamination cycle was performed by allowing the massage plate to move forward to the ostomy bag and massage the output containing ostomy bag, resulting in a controlled contamination of the surfaces within the ostomy bag, including the filter construction.

When the cycle was finished, the ostomy bag was again inflated to 10 mbar and the flow through the filter construction was determined as described above.

This contamination step was repeated until the filter construction was clogged. The flow through the filter construction was determined at 10 mbar for each contamination cycle.

Different test series were performed.

In a first series of tests, ostomy bags with a filter construction according to this invention was tested and compared to ostomy bags with a reference filter construction. The filter construction according to this invention included a pre-filter element having a generally circular periphery of about 110 mm and having an inspection hole of about 60 mm cut off centre. The filter construction is further provided with a hole for a deodorising element of about 30 mm positioned in the lower part of the pre-filter element. The reference filter construction comprises a pre-filter of porous material 50 mm×10 mm×3 mm and a deodorising filter of carbonised foam 30 mm×7 mm×3 mm.

The ostomy bags according to this invention were of two different kinds. In series 1.1., the ostomy bags were bags adapted to be used with a colostomy and were thus provided with 96 holes functioning as gas-inlets. The holes were punched with a needle with a diameter below 1 mm; approximately 0.5 mm. 6 holes of approximately 1 mm in diameter were included. In this series, four ostomy bags according to this invention and five reference bags were tested. All bags (the sample bags and the reference bags) were filled with a test-medium which is comparable to porridge like the output mentioned earlier. The table below shows how many contamination cycles each bag were subjected to before there was no flow through the bag.

TABLE 1

| Ostomy bag | colo-sample 1 | colo-sample 2 | colo-sample 3 | colo-sample 4 |
|---|---|---|---|---|
| contamination cycles | 11 | 9 | 15 | 16 |
| ostomy bag | ref. 1 | ref. 2 | ref. 3 | ref. 4 | ref. 5 |
| contamination cycles | 2 | 1 | 1 | 1 | 2 |

From Table 1 above it appears that the ostomy bags according to this invention (sample 1 to sample 4) and filled with colo-like output to a great extent out-perform the reference bags (ref. 1 to ref. 5). In average, the ostomy bags according to this invention lasted 13 contamination cycles compared to only 1-2 cycles for the reference bags.

Series 1.2 comprises ostomy bags according to the invention and adapted to be used with an ileostomy. These bags were thus provided with 2 holes of approximately 1 mm in diameter functioning as gas-inlets. In this series, four ostomy bags according to this invention and five reference bags were tested. All bags (the sample bags and the reference bags) were filled with a test-medium which is comparable to syrupy output mentioned earlier. The table below shows how many contamination cycles each bag were subjected to before there was no flow through the bag.

TABLE 2

| Ostomy bag | ileo-sample 1 | ileo-sample 2 | ileo-sample 3 | ileo-sample 4 |
|---|---|---|---|---|
| contamination cycles | 12 | 13 | 11 | 12 |
| ostomy bag | ref. 1 | ref. 2 | ref. 3 | ref. 4 | ref. 5 |
| contamination cycles | 1 | 1 | 1 | 1 | 1 |

From Table 2 above it appears that the ostomy bags according to this invention (sample 1 to sample 4) and filled with ileo-like output to a great extent out-perform the reference bag (ref. 1 to ref. 5). In average, the ostomy bags according to this invention lasted 12 contamination cycles compared to only 1 cycle for the reference bag.

The $2^{nd}$ series of tests relates to the influence of size of holes. Only ileostomy bags were tested in this series because output from a colostomy may include both thin and thicker output. Therefore, the influence of size of holes is most important to test for bags including only the thin output. In series 2.1 ileostomy bags with 2 mm holes were tested. These results are compared to series 2.2 comprising ileostomy bags with 1 mm holes. Table 3 below shows the results of these two test series.

TABLE 3

| | ostomy bag | ileo-sample 1 | ileo-sample 2 | ileo-sample 3 | ileo-sample 4 |
|---|---|---|---|---|---|
| Series 2.1 2 mm holes | contamination cycles | 10 | 8 | 9 | 9 |
| Series 2.2 1 mm holes | contamination cycles | 4 | 3 | 4 | 4 |

The results in the table above show that 1 mm holes are less preferable than 2 mm holes. This may be because the thin output might be able to clog the smaller holes (of 1 mm) and because the filter construction only comprises 2 gas-inlets, it is very important that both of them are kept open. The 2 mm holes will not be clogged by thin output. Furthermore, the large pre-filter element is able to handle (to contain) the output entering into the pre-filter element—at least for approximately 9 cycles (series 2.1).

DETAILED DESCRIPTION OF THE DRAWING

FIG. 1 illustrates an ostomy appliance 1 according to one embodiment of the invention. The ostomy appliance comprises a pouch having a rear wall 2 and a front wall 3, that are welded together along their rim (not shown). The rear wall 2 has a waste inlet opening 4, which in this embodiment is surrounded by a skin-friendly adhesive 5, thus this is a so-called one-piece appliance. The stoma 6 is also shown. The filter construction 10 in the ostomy appliance comprises a first foil layer 11, and a second foil layer 12, welded together along their outer contour 13. The foil layers 11, 12 are provided with numerous holes 14 functioning as gas-inlets to the filter construction 10. The pre-filter element 15 is, in this embodiment, a generally annular element with a cut-out 16 for the deodorising filter 17. The deodorising filter 17 is in this embodiment a disc-shaped element. The deodorising filter 17 is enclosed in gas- and liquid-impermeable foils 18, 19. These foils 18, 19 are welded or glued to the foil layers 11, 12 enclosing the entire filter construction 10 and furthermore welded or glued to the surfaces of the deodorising filter 17. Thus, gas flowing in the filter construction is confined to flow through the deodorising filter from the periphery towards the centre. The filter construction 10 also includes a membrane 20 placed at the central part of the deodorising filter 17, so as to cover the gas-outlet 22 from the filter construction. In this embodiment, the gas-outlet 22 is surrounded by a filter flange 21, which is permanently attached to the filter construction 10 and welded to the ostomy appliance 1. Thereby, the filter construction 10 is attached to the ostomy appliance 1. The gas-outlet 22 leads deodorised gas to the outside environment through the vent 23 in the front wall 3 of the pouch. The drawing is not to scale.

FIGS. 2 and 3 illustrate another embodiment of an ostomy appliance 101 according to the invention. FIG. 2 illustrates a view of the ostomy appliance 101 seen from the rear side and FIG. 3 illustrates a view seen in cross-section. The ostomy appliance 101 may be provided in at least three sizes, MINI, MIDI and MAXI (as shown in FIG. 2). The three sizes are shown to illustrate the relative size relationship between the filter construction 110 and the ostomy appliance 101 for these three sizes. This embodiment differs from the embodiment of FIG. 1 in that the pre-filter element 115 includes an inspection window 125 large enough to view the stoma 6 and the area immediately around the stoma 6. The inspection window 125 is made of the same foils 111, 112 that are used to enclose the filter construction 110 which is possible because the foils 111, 112 in this embodiment are transparent. Thus the inspection window 125 is made by welding the foils together in a circle 126 so as to prevent any matter in the filter construction entering into and obstructing the view through the inspection window 125. It is to be understood that the filter construction of the present invention may also be incorporated in other sizes, kinds and shapes of bodily waste collecting bags.

The gas-inlets 114 to the filter construction are numerous and generally placed around the inspection window 125. The lower part of the pre-filter element 115 includes a cut-out 116 for the deodorising filter 117. The deodorising filter 117 is enclosed in foils 118, 119 so as to ensure that the gas is confined to travel transversely through the deodorising filter from the periphery towards the centre, just like the embodiment in FIG. 1. Like with the filter construction of FIG. 1, this filter construction 110 is also provided with a membrane 120. The filter construction 110 may be permanently attached to the pouch by welding a filter flange 121 to the front wall of the pouch, as described under FIG. 1.

The filter construction 110 is further provided with carrying means 130, 131 of foil. These carrying means 130, 131 may be welded with the rim of the pouch and assist in carrying and controlling the position of the filter construction 110.

Figure 4:
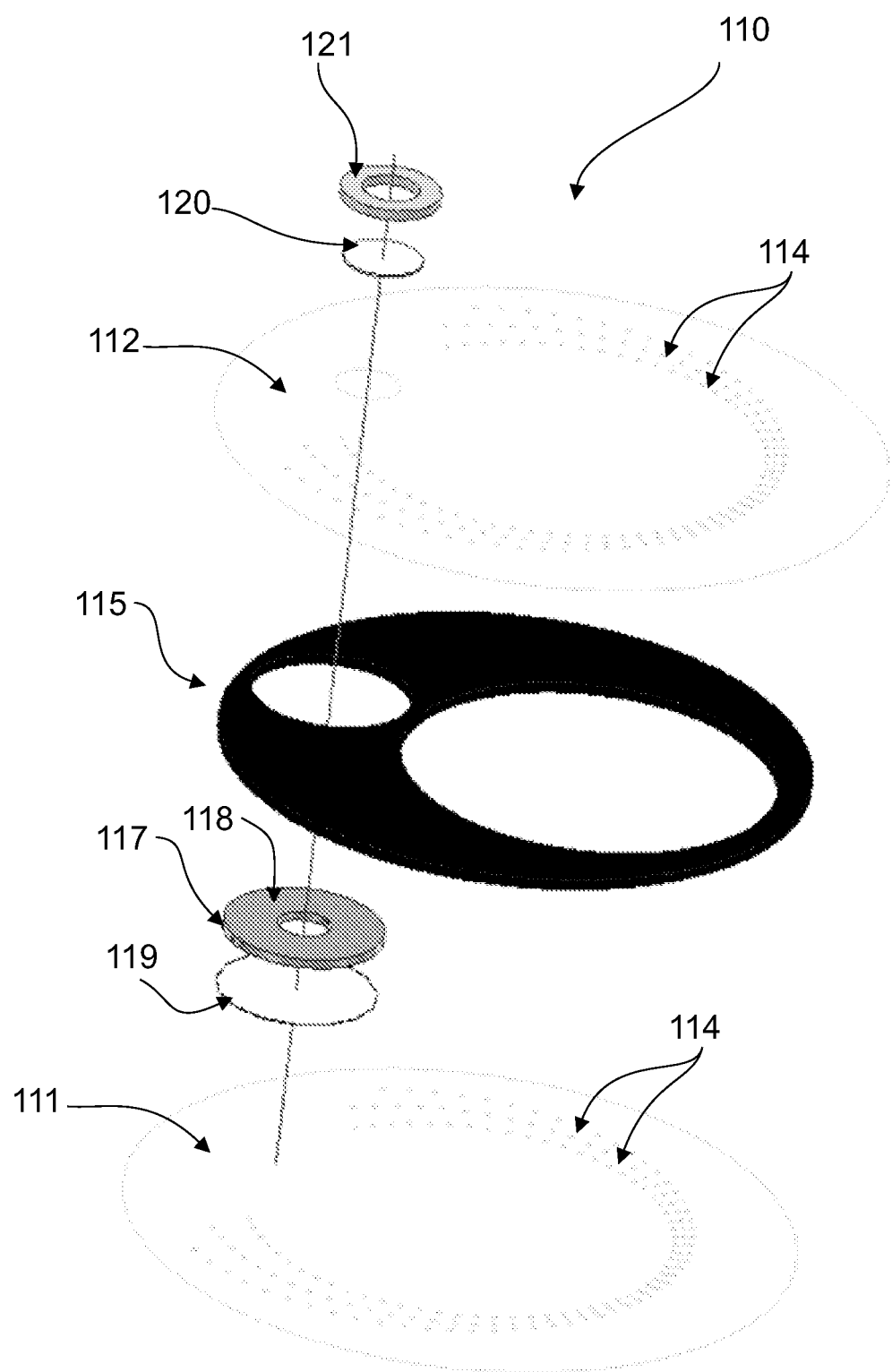
FIG. 4 illustrates an exploded view of the filter construction of the embodiment in FIGS. 2 and 3.

FIG. 4 illustrates an exploded view of the filter construction 110 of FIGS. 2 and 3—however, the carrying means for controlling the filter construction are not shown. The filter construction 110 includes a filter flange 121, a membrane 120, a second foil layer 112 with the numerous holes providing gas-inlets 114, a pre-filter element 115 of foam with a cut-out 116 for the deodorising filter, a deodorising filter 117 with a foil 118 at the top, a second foil 119 so foils 118, 119 together enclose the deodorising filter and finally, the first foil layer 111 also being provided with numerous holes as gas-inlets 114. The positioning of the holes fulfils the above-mentioned requirements for the distances between holes.

Figure 5:
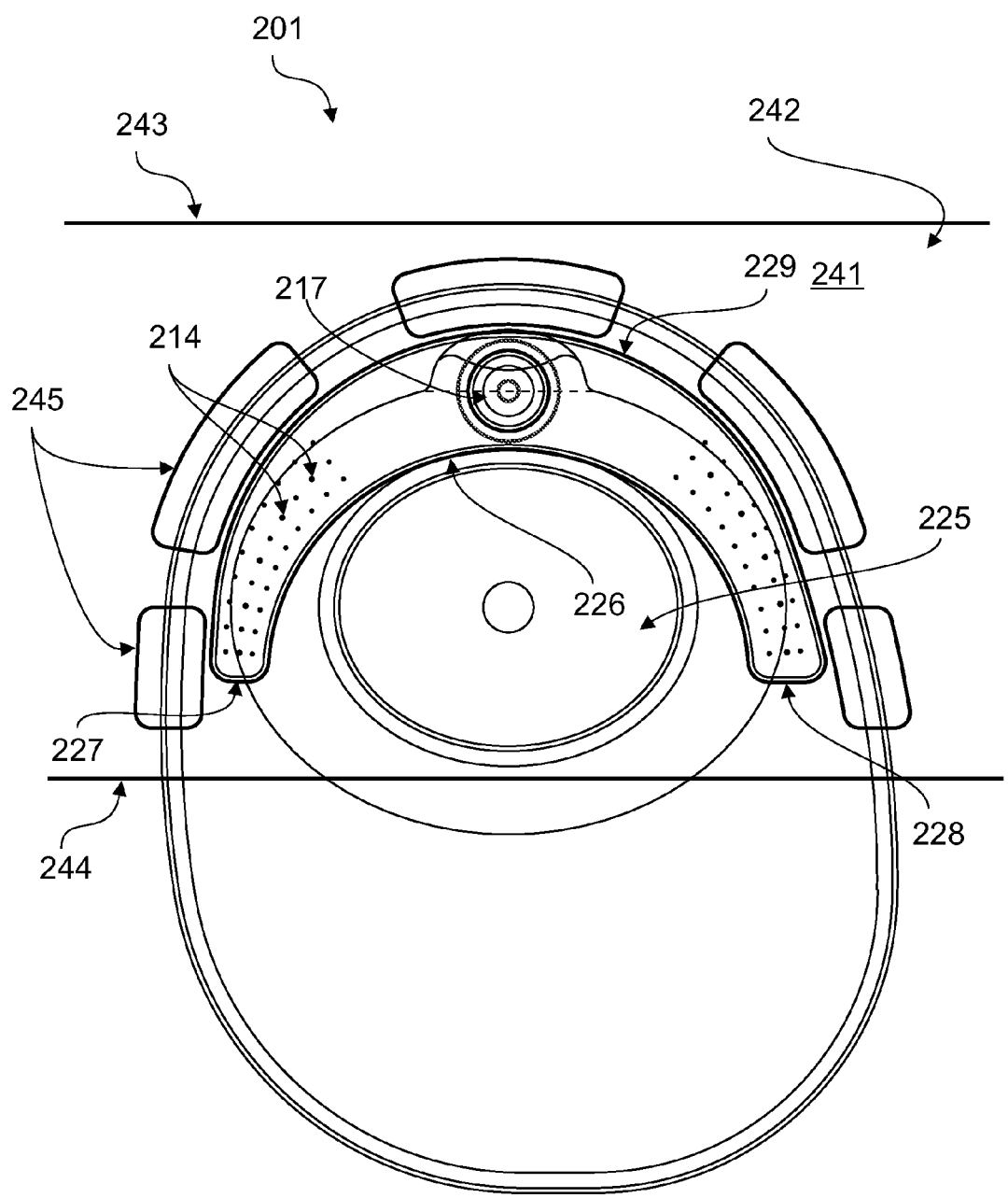
FIG. 5 illustrates yet another embodiment of an ostomy appliance according to the invention.

FIG. 5 illustrates an ostomy appliance 201 according to the invention, wherein the pre-filter element 215 in the filter-construction 210 is generally banana-shaped and placed above the waste-inlet opening 204. The pre-filter element comprises a first 211 and second 212 foil layer, which during manufacturing forms part of larger foil lengths 241, 242. The two larger foils lengths 241, 242 extend from a top edge 243 towards a lower edge 244. The top edge 243 is placed above the upper rim of the ostomy bag 201 and extends below the lower edge of the filter construction 210. Likewise, the larger foils 241, 242 extend beyond the sides of the pouch. In these larger foils 241, 242 the filter construction 210 including the inspection window 225 is provided by welding the foils at the inner periphery 226 of the pre-filter element (the inner curved side of the banana-shape), along the lower edges 227, 228 of the pre-filter element and at the outer periphery 229 of the pre-filter element (the outer curved side of the banana-shape). The holes 245 are used for controlling the filter construction during manufacturing. When the appliance 201 is to be manufactured this finished filter-construction is attached to any of the front wall or rear wall during a separate welding process or to the front and rear wall when welding the rim of the pouch.

Foil lengths such as the ones shown in FIG. 5 may also be used for manufacturing the embodiments of FIGS. 1 to 4.

Figure 6:
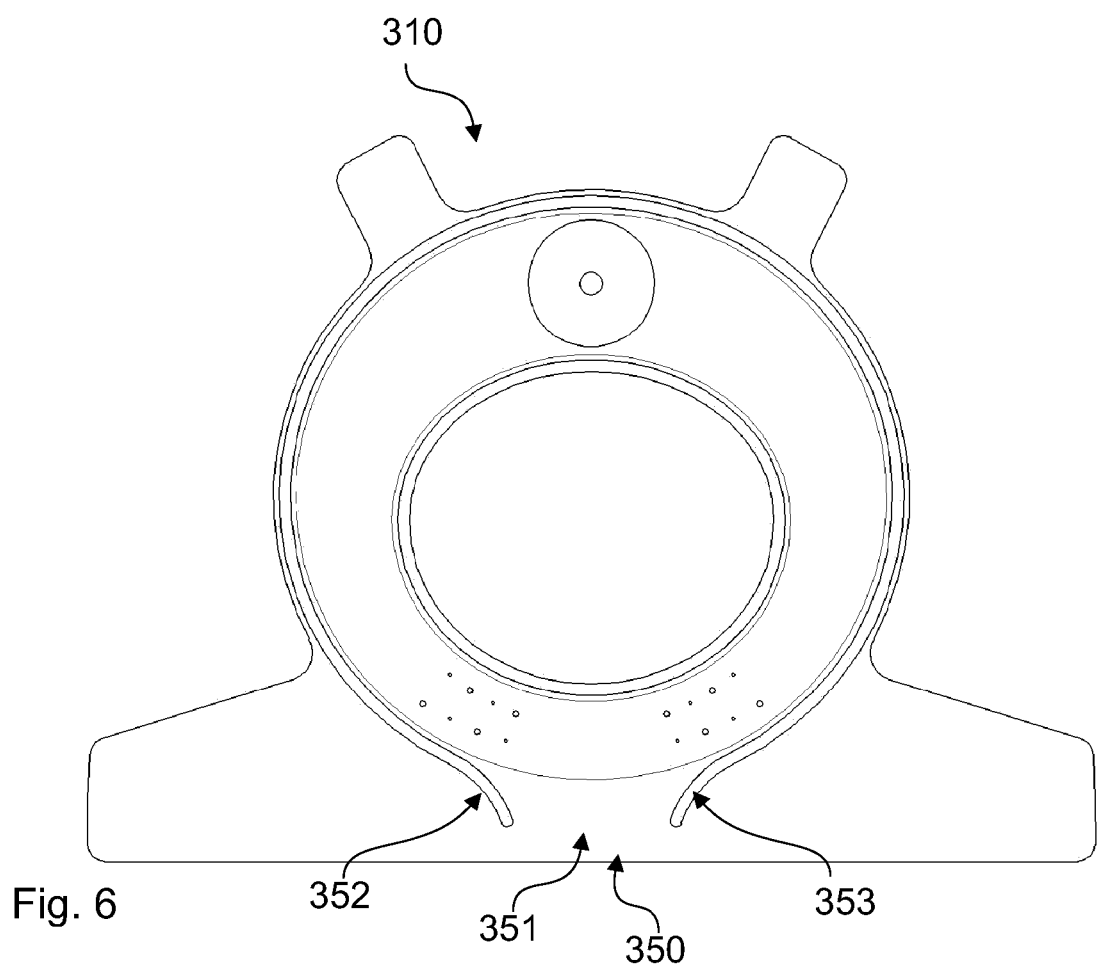
FIG. 6 illustrates an embodiment of a filter construction provided with a drainage opening.

FIG. 6 illustrates a filter construction 310, which is provided with a drainage opening 350. The drainage opening 350 comprises a one-way valve 351 with two foil flaps 352, 353 that provide a one-way path out of the filter construction 310. During normal use, when the filter construction is positioned with the drainage opening 350 facing downwards, liquid output in the filter construction 310 will travel towards the drainage opening 350 and exit out through the one-way valve 351 and into the pouch. Because of the one-way function of the valve 350, liquid output in the pouch will be prevented from entering through the valve 350 and into the filter construction 310.

Figure 7A:
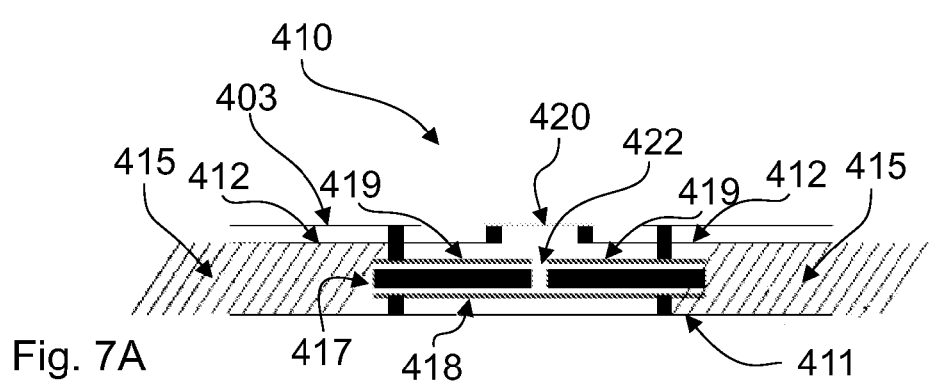
FIG. 7 illustrates an embodiment of the deodorising filter enclosed in a three-layer foil structure.
Figure 7B:
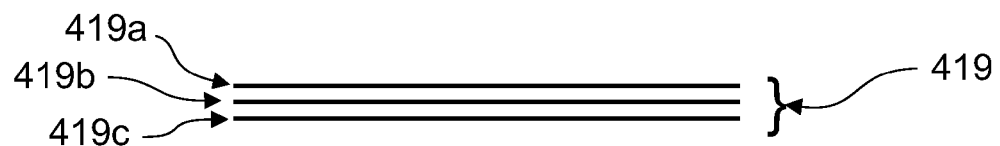

FIG. 7 illustrates part of a filter construction 410, in which the deodorising filter 417 is enclosed in a three-layer foil structure 418, 410. FIG. 7A illustrates part of the filter construction and FIG. 7B illustrates the three layers constituting the foils 418 and 419. The three-layer foil structure comprises an outer layer 419a, an intermediate layer 419b and an inner layer 419c. The outer layer 419a (facing outwards from the deodorising filter) and the inner layer 419c (facing inwards towards the deodorising filter) may be made of the same material, for example EVAPE and the intermediate layer 419b may be made of PA. As mentioned earlier, the foil structure 419 facing towards the gas exit has to be liquid- and gas-impermeable, whereas the foil structure 418 does not need to be gas-impermeable because it faces inwards in the pouch in use. FIG. 7A illustrates part of the filter construction 410 including the pre-filter element 415 and the foils 411, 412 enclosing the filter construction. The gas outlet 422 from the deodorising filter may be covered with a membrane 420 as illustrated in the figure. The foil structure 419 may be welded to the front wall 403 of the pouch.

Figure 8:
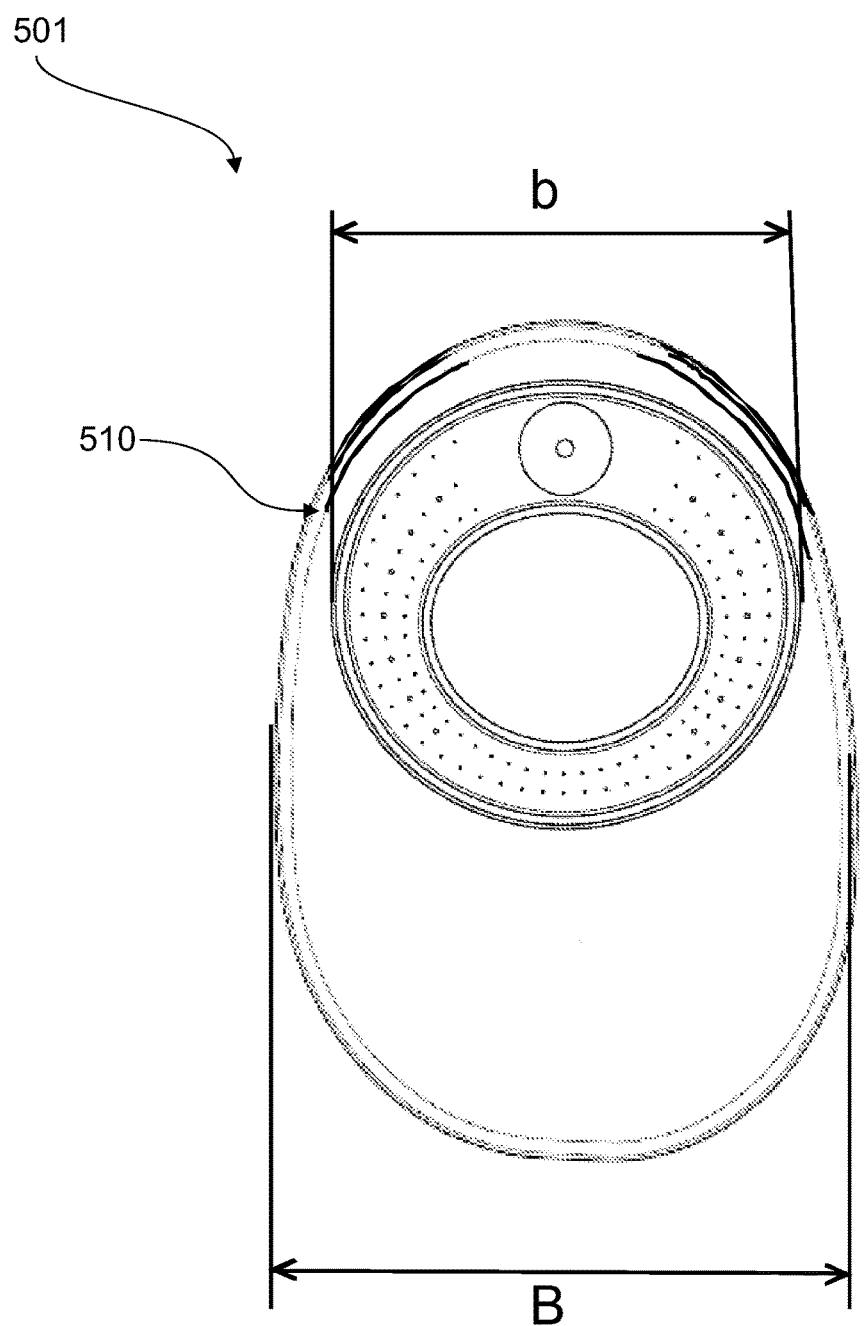
FIG. 8 illustrates an embodiment of an ostomy appliance according to the invention.

FIG. 8 illustrates an ostomy appliance 501 according to the invention. The ostomy appliance 501 is in FIG. 8 shown in the first configuration when the pouch is neither distended nor inflated. The ostomy appliance 501 includes a filter construction 510 according to the invention. The filter construction has a width b that is at least 60% (preferably at least 80%) of the width B of the pouch in the first configuration of the pouch. The width means, in this connection, the dimension in the transverse direction of the bag. Both widths are measured from the outermost boundary at one side to the outermost boundary transversely across the pouch (or filter construction).

Figure 9:
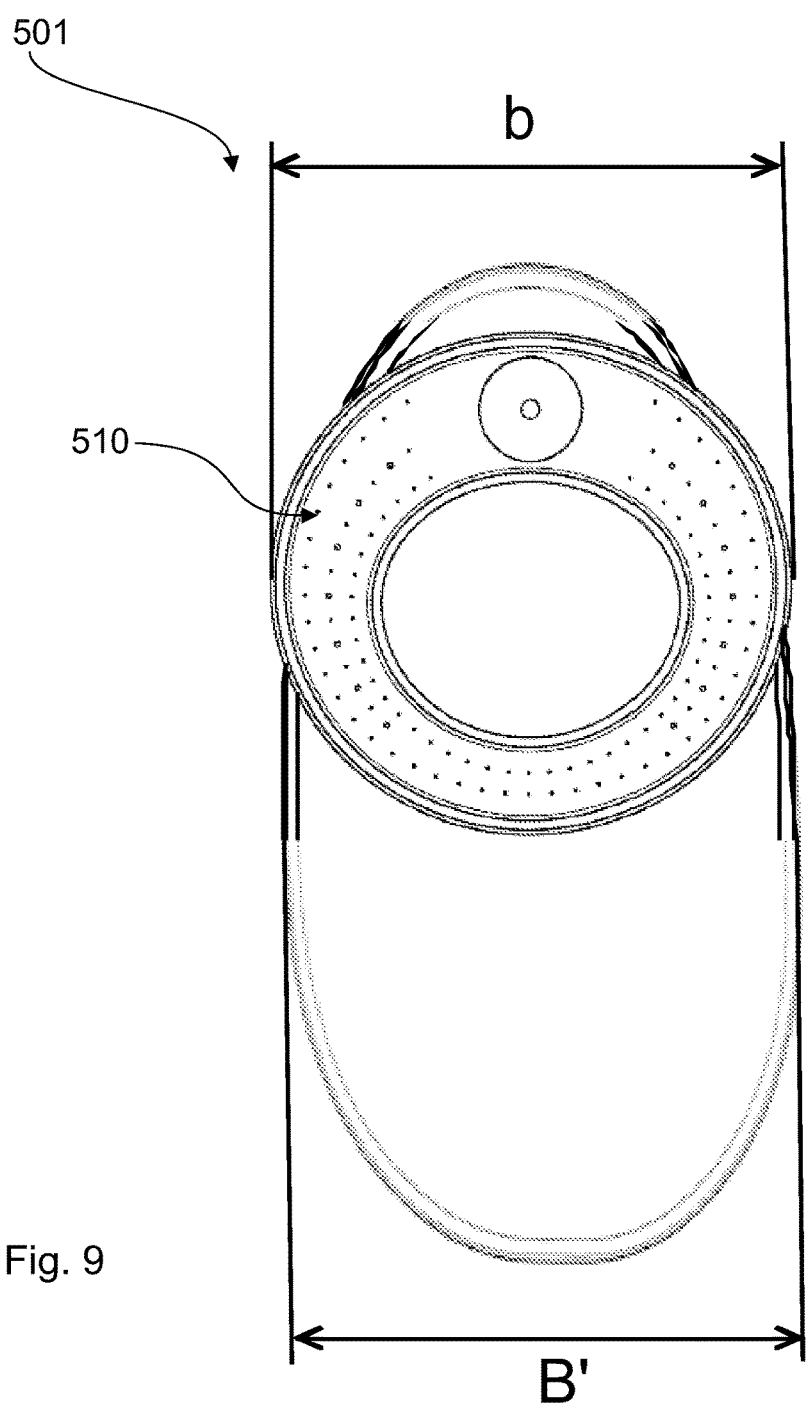
FIG. 9 illustrates the same embodiment of the ostomy appliance according to the invention; however, in FIG. 9, the appliance is illustrated in the second configuration.

FIG. 9 illustrates an ostomy appliance 501 according to the invention shown in the second configuration, when the pouch is distended or inflated. As it appears from the figure the width B' of the pouch in this configuration has been reduced so that it is now smaller than the width b of the filter construction.

Figure 10:
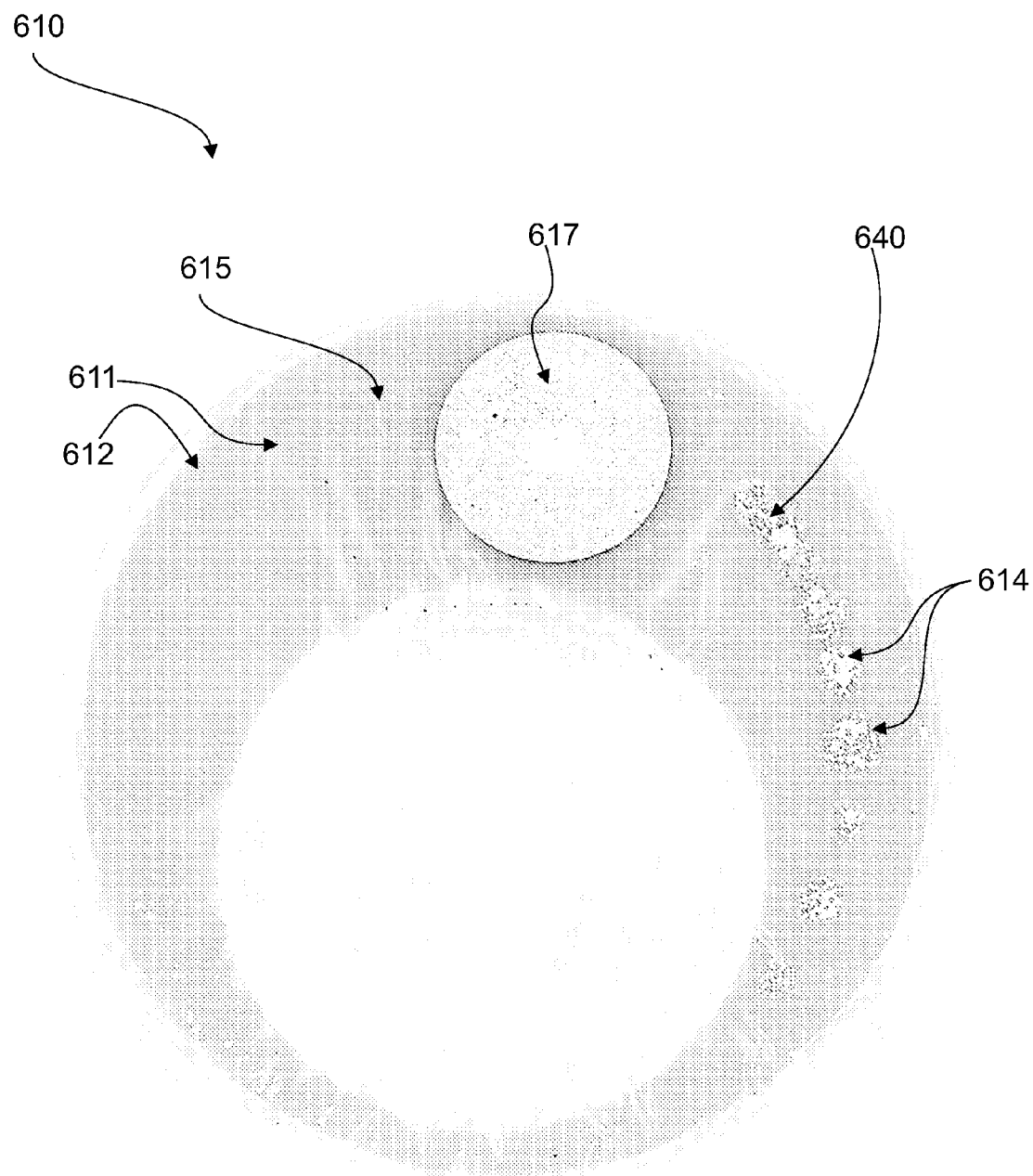
FIG. 10 illustrates a filter construction for use in an ostomy appliance according to the invention.

FIG. 10 illustrates another filter construction 610 according to the invention. The filter construction comprises a first layer of foil 611 and a second layer of foil 612. Enclosed in the foil layers is a pre-filter 615 of foam. The two foil layers 611, 612 are provided with gas-inlets 614 in the form of holes. The filter construction 610 also includes a deodorising filter 617. From the figure it appears that output 640 that has entered into the pre-filter 615 travels only a certain distance into the pre-filter. Therefore, if the gas-inlets 614 are positioned with a larger distance between each other than the maximum penetration length of the output, then output will not be able to travel from one gas-inlet to a neighbouring gas-inlet.

Figure 11:
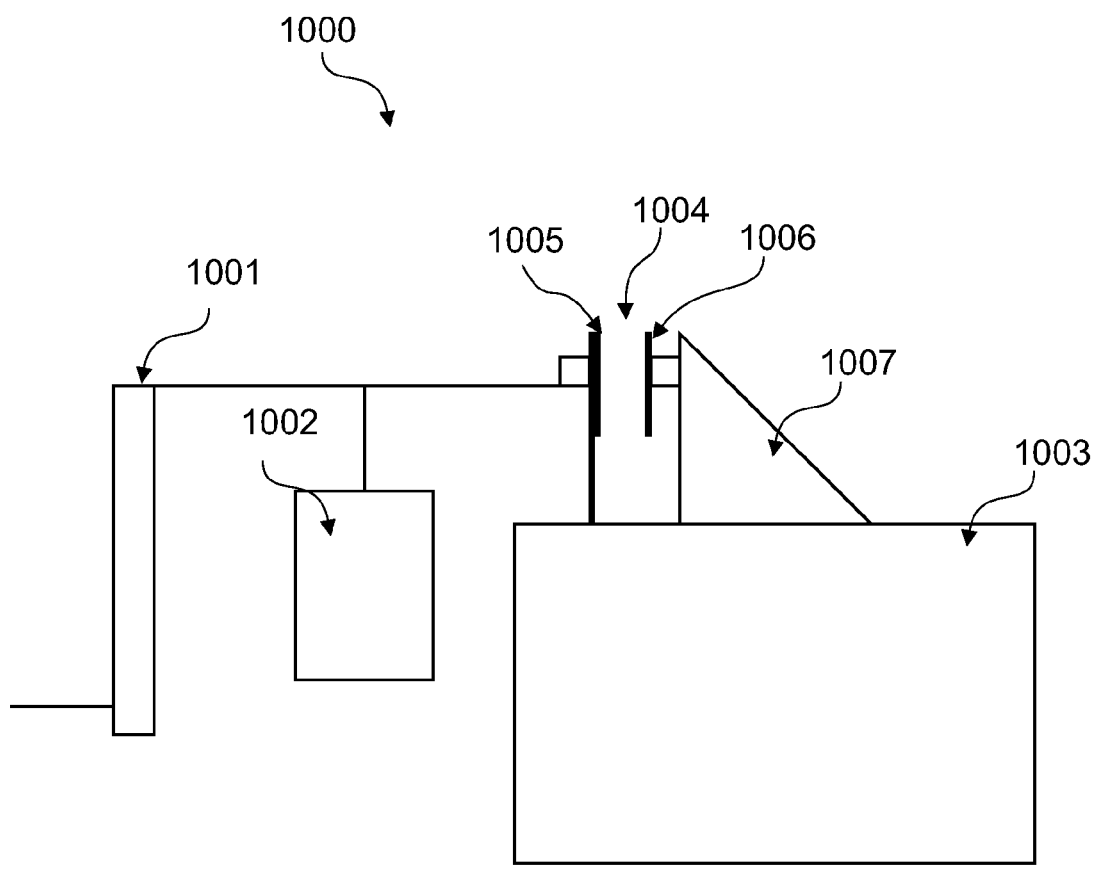
FIG. 11 illustrates a test-setup used for testing pouches of ostomy appliances according to the invention.

FIG. 11 illustrates a schematic drawing of the filter tester apparatus 1000 used in the Example mentioned above. The filter tester apparatus 1000 comprises a flow-controller 1001 for measuring the flow through the filter construction and a differential pressure-meter 1002 for measuring the pressure in the ostomy bag. Such flow-controller and pressure-meter are well-known in the art. The filter tester unit 1003 is a control unit able to apply a controlled massaging and shaking of an ostomy bag. The ostomy bag (not shown) is during testing held in the ostomy bag holder 1004 comprising a holder plate, 1005, 1006 at each side of the bag. The filter tester unit 1003 controls a massaging plate 1007 to apply the controlled massaging of the bag.

Figure 12:
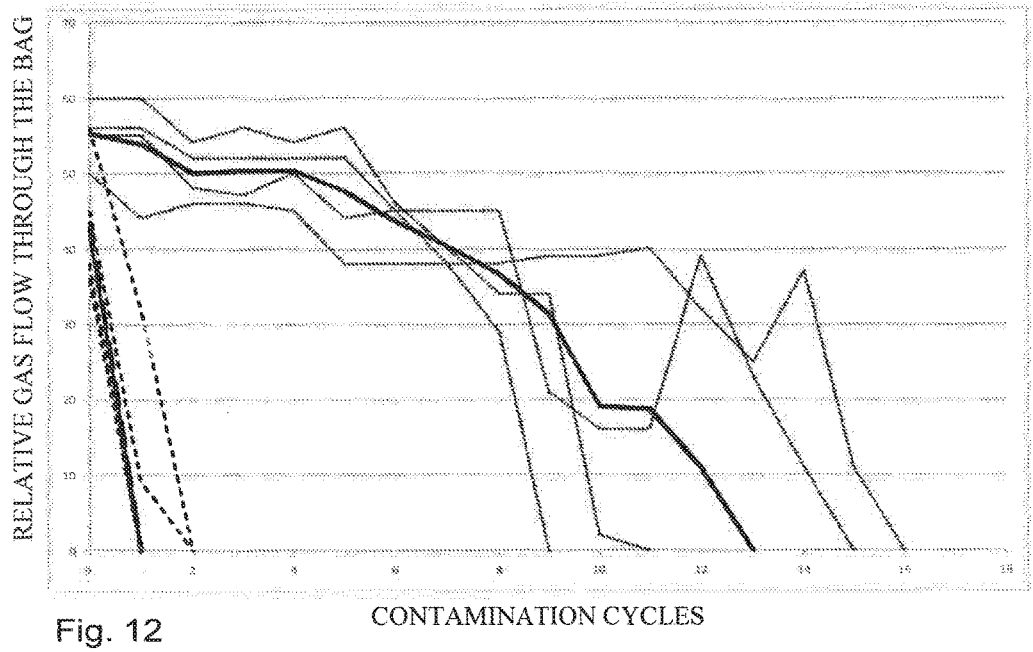
FIGS. 12-14 illustrate results of testing of ostomy appliances according to the invention.
Figure 13:
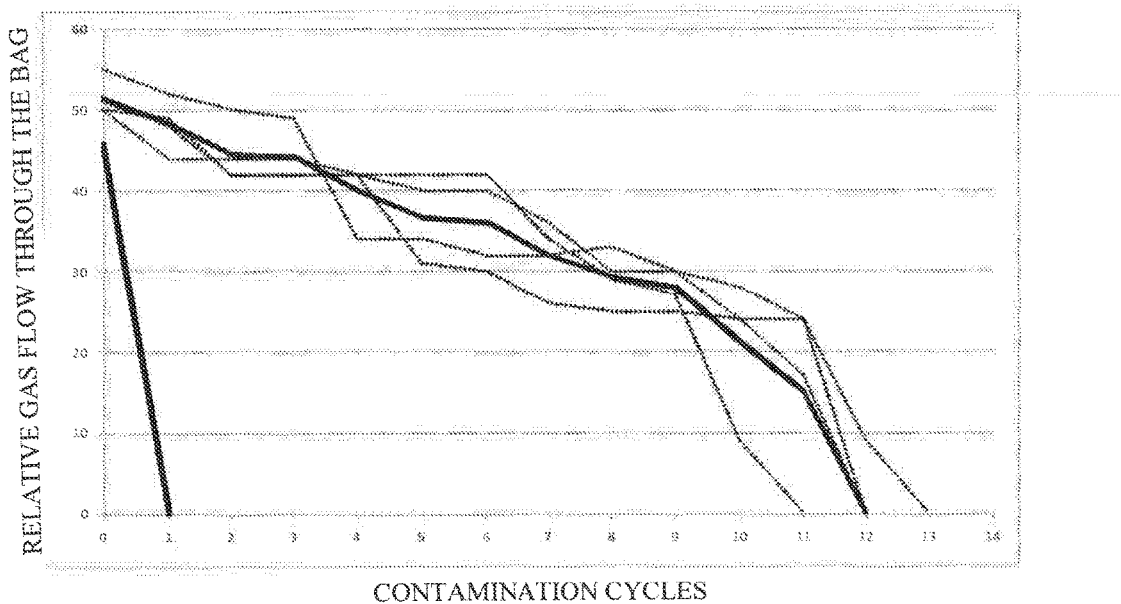

FIGS. 12 and 13 illustrate the results of test-series 1. FIG. 12 illustrates results of testing on colostomy bags—corresponding to test-series 1.1 described above—and FIG. 13 illustrates results of testing on ileostomy bags—corresponding to test-series 1.2 described above. The difference between ostomy bags according to the invention and ostomy bags provided with standard filters (described above) is evident. In both figures the dotted lines show results of testing of ostomy bags according to the invention and the dashed lines (to the left in figures) show results of testing ostomy bags with standard filters. The full lines between the dotted and dashed lines illustrate the average values. In FIG. 13 only the average line for the standard filter is visible, because all filter lasted only 1 cycle. Thus for colostomy bags, in FIG. 12 it is illustrated that an ostomy bag according to the invention—in average lasts 13 cycles of contamination before the flow through the bag is below an acceptable level. This is to be compared to an average value for an ostomy bag with a standard filter lasting only 1-2 cycles. For ileostomy bags, FIG. 13 shows that an average ostomy bag according to the invention lasts 12 cycles. An average ostomy bag with a standard filter lasts only 1 cycle.

Figure 14:
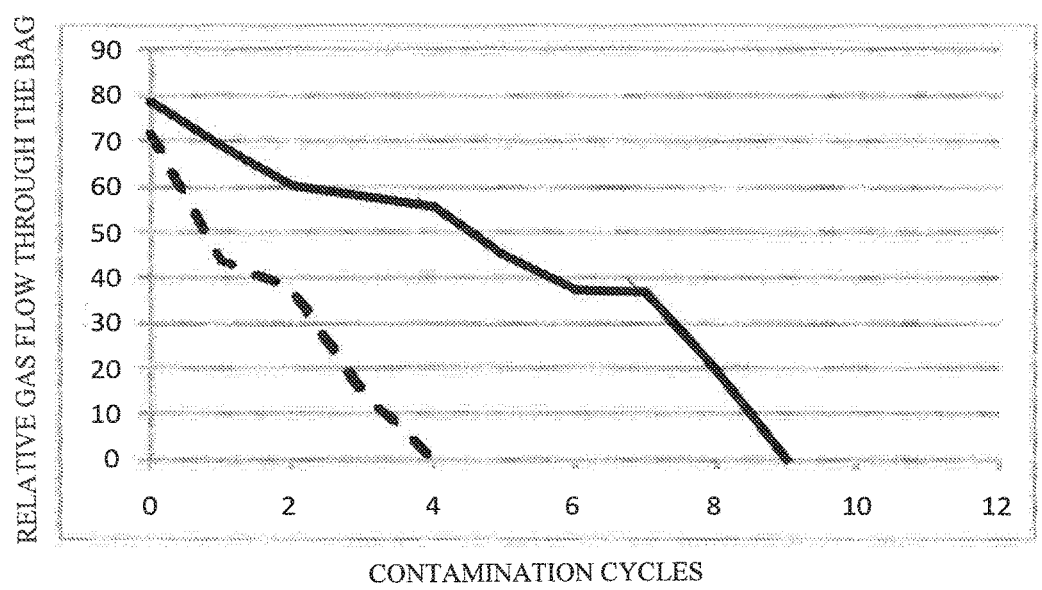

FIG. 14 illustrates test results corresponding to test-series 2 above. FIG. 14 reveals that using holes of only 1 mm in diameter (the dashed line) has a negative influence on ileostomy bags. The flow diminishes faster and the bags last shorter than bags with 2 mm holes (the full line).

The invention claimed is:

1. An ostomy appliance comprising:
   a body-waste collection pouch having a waste opening adapted for placement over a stoma to allow body waste output to enter an interior of the pouch and a vent opening provided in a wall of the pouch to allow gas to exit the pouch; and
   a filter construction secured around the vent opening to filter odor from the gas, with the filter construction comprising:
      a first foil layer connected to a second foil layer to provide an enclosure having an outer contour,
      a pre-filter element contained in the enclosure and a gas-outlet formed in the second foil layer on a gas-outlet side of the enclosure,
   wherein a portion of the second foil layer of the filter construction is attached to the wall of the pouch so that the gas-outlet of the filter construction communicates with the vent opening of the pouch and a substantial portion of an outer surface of the second foil layer is adjacent to and separated from the wall of the pouch;
   wherein holes are formed in the first foil layer to provide multiple gas-inlets to the pre-filter element and the second foil layer is gas impermeable and includes an array of holes formed in the second foil layer to provide multiple gas-inlets to the pre-filter element on a side of the enclosure opposite from the first foil layer.

2. The ostomy appliance of claim 1, wherein each of the first foil layer and the second foil layer is substantially parallel with a front wall and a rear wall of the pouch with the first layer of foil facing the rear wall and the second layer of foil facing the front wall of the pouch.

3. The ostomy appliance of claim 1, wherein a number of the multiple gas-inlets is more than 50.

4. The ostomy appliance of claim 1 further comprising a deodorizing filter.

5. The ostomy appliance of claim 4, wherein the deodorizing filter is positioned on an outside surface of the pouch so that it communicates with the vent opening in the pouch.

6. The ostomy appliance of claim 4, wherein the deodorizing filter is positioned inside the pouch communicating with the vent opening and outside of the enclosure of the filter construction communicating with the gas-outlet.

7. The ostomy appliance of claim 1, wherein the filter construction is adapted to crumble when the pouch is filled.

8. The ostomy appliance of claim 1, wherein a distance between two gas-inlets is such that liquid cannot travel from one gas-inlet to a neighboring gas-inlet within a time of use of the ostomy appliance.

9. The ostomy appliance of claim 1, wherein the enclosure of the filter construction comprises a drainage opening facing downwards within the ostomy appliance.

10. The ostomy appliance of claim 9, wherein the drainage opening comprises a one-way valve.

11. The ostomy appliance of claim 1, wherein the filter construction is attached to a filter flange surrounding the gas-outlet.

12. The ostomy appliance of claim 1, wherein the second foil layer of the filter construction is directly welded to the wall of the pouch with a majority of surface area of the second foil layer not attached to the wall of the pouch.

13. The ostomy appliance of claim 1, wherein the filter construction further includes a membrane positioned at the gas outlet.

14. The ostomy appliance of claim 1, wherein the pre-filter element comprises a disc-shaped cut-out to match a disc-shaped deodorizing filter.

15. The ostomy appliance of claim 1, wherein the pre-filter element comprises a banana-shaped cut-out to match a banana-shaped deodorizing filter.

16. The ostomy appliance of claim 1, wherein an area of the pre-filter element is at least 20% of an area of the pouch as measured in a plane of the pouch.

17. The ostomy appliance of claim 1, wherein the filter construction includes an inspection window.

18. The ostomy appliance of claim 17, wherein the waste opening is opposite of the vent opening, with the pre-filter element provided as a generally disc-shaped element having a circular hole with a diameter of at least a diameter of the waste opening, and the inspection window is provided in the pre-filter element.

19. The ostomy appliance of claim 17, further comprising:
   a filter flap configured to close the vent opening.

20. The ostomy appliance of claim 1, wherein the filter construction has a width in a transverse direction that is at least 60% of a width of the pouch in the transverse direction.

21. The ostomy appliance of claim 1, wherein the filter construction is attached to the pouch at a location closer to a top of the pouch than a bottom of the pouch.

22. The ostomy appliance of claim 1, wherein the vent opening is provided at a location closer to a top of the pouch than a bottom of the pouch.

23. The ostomy appliance of claim 1, wherein a first surface area of the pre-filter element in a plane parallel to the front wall and the rear wall is 10-90% of a second surface area of the front wall or the rear wall.

24. The ostomy appliance of claim 1, wherein the multiple gas-inlets are formed as a matrix of holes formed over a portion of a surface area of the first foil layer and formed over a portion of a surface area of the second foil layer.

25. The ostomy appliance of claim 1, wherein a majority of the first foil layer and a majority of the second foil layer is not attached to the pouch such that the filter construction is cantilevered in the pouch relative to the vent opening.

26. The ostomy appliance of claim 1, wherein a majority of the first foil layer and a majority of the second foil layer is not attached to the pouch such that the filter construction is free-hanging within the interior of the pouch.

27. The ostomy appliance of claim 1 wherein the pre-filter element includes an opening cut-out of the pre-filter element and the ostomy appliance further comprises a deodorizing filter inserted into the opening cut-out of the pre-filter element.

28. The ostomy appliance of claim 1 wherein the pre-filter element includes an opening cut-out of the pre-filter element and the ostomy appliance further comprises a deodorizing filter inserted coaxially in the opening cut-out of the pre-filter element.

29. The ostomy appliance of claim 1 wherein at least one of the array of holes include holes formed to have a hole diameter in a range from 0.1 mm to 2.0 mm.

30. The ostomy appliance of claim 1 wherein the first foil layer is gas impermeable and includes a second array of holes formed in the first foil layer to provide the multiple gas-inlets to the pre-filter element.

\* \* \* \* \*